US009464097B2

(12) United States Patent
Nolan

(10) Patent No.: US 9,464,097 B2
(45) Date of Patent: Oct. 11, 2016

(54) GOLD COMPLEXES

(75) Inventor: Steven P. Nolan, St Andrews (GB)

(73) Assignee: UNIVERSITY COURT OF THE UNIVERSITY OF ST. ANDREWS, St. Andrews (GB)

( * ) Notice: Subject to any disclaimer, the term of this patent is extended or adjusted under 35 U.S.C. 154(b) by 733 days.

(21) Appl. No.: 13/580,772

(22) PCT Filed: Mar. 2, 2011

(86) PCT No.: PCT/GB2011/000284
§ 371 (c)(1),
(2), (4) Date: Sep. 25, 2012

(87) PCT Pub. No.: WO2011/107736
PCT Pub. Date: Sep. 9, 2011

(65) Prior Publication Data
US 2013/0035322 A1 Feb. 7, 2013
US 2016/0016976 A2 Jan. 21, 2016

(30) Foreign Application Priority Data
Mar. 2, 2010 (GB) .................................. 1003483.3

(51) Int. Cl.
C07F 1/12 (2006.01)
B01J 31/22 (2006.01)
B01J 31/02 (2006.01)
B01J 31/24 (2006.01)

(52) U.S. Cl.
CPC .............. *C07F 1/12* (2013.01); *B01J 31/0211* (2013.01); *B01J 31/2273* (2013.01); *B01J 31/24* (2013.01); *B01J 2531/18* (2013.01)

(58) Field of Classification Search
CPC ..................................................... C07F 1/12
See application file for complete search history.

(56) References Cited

U.S. PATENT DOCUMENTS

2007/0240797 A1 10/2007 Mendenhall
2009/0018330 A1 1/2009 Molt et al.
2013/0085276 A1 4/2013 Nolan et al.

OTHER PUBLICATIONS

Sini et al. "Preferential C-Binding versus N-Binding in Imidazole Depends on the Metal Fragment Involved" Inorganic Chemistry, 2002, vol. 41, pp. 602-604.*
Marion et al. "[(NHC)AuI]-Catalyzed Formation of Conjugated Enones and Enals: An Experimental and Computational Study" Chemistry A European Journal, 2007, vol. 13, pp. 6437-6451.*
Arcadi, Antonio, "Alternative Synthetic Methods through New Developments in Catalysis by Gold", Chem. Rev., 2008, vol. 108, pp. 3266-3325.
Bayler, Angela et al., "Synthesis and Structure of Binuclear Single-Bridged Bis[(phosphane)gold(I)]halogenonium Complexes", Chem. Ber./Recueil, 1997, vol. 130, pp. 115-118.
Bender, Christopher F., et al., "Room Temperature Hydroamination of N-Alkenyl Ureas Catalyzed by a Gold(I) N-Heterocyclic Carbene Complex", Organic Letters, 2006, vol. 8, No. 23, pp. 5303-5305.
Blair, Larry K., et al., "Acidities of Anilines and Toluenes", J. Org. Chem., 1977, vol. 42, No. 10,pp. 1817-1819.
Boogaerts, Ine I.F., et al., "Carboxylation of C-H Bonds Using N-Heterocyclic Carbene Gold(I) Complexes", J.AM. Chem. Soc., 2010, vol. 132,pp. 8858-8859.
Bordwell, Frederick G., et al., "Acidities and Hydrogen Bonding of Phenols in Dimethyl Sulfoxide", J. Org. Chem., 1984, vol. 49, pp. 1424-1427.
Cinellu, Maria Agostina et al., "Synthesis and Characterization of Mononuclear Amidogold(III) Complexes—Crystal Structure of [Au(N$_2$C$_{10}$H$_7$(CMe$_2$C$_6$H$_4$)-6] (NHC$_6$H$_3$Me$_2$-2,6)][PF$_6$]-Oxidation of 4-Methylaniline to Azotoluene", Eur. J. Inorg. Chem., 2003, pp. 2304-2310.
de Fremont, Pierre et al., "Synthesis and Structural Characterization of N-Heterocyclic Carbene Gold(I) Complexes", Organometallics, 2005, vol. 24, pp. 2411-2418.
Diez-Gonzales, Silvia et al., "N-Heterocyclic Carbenes in Late Transition Metal Catalysis", Chem. Rev., 2009, vol. 109, pp. 3612-3676.
Gaillard, Sylvain et al., "A N-Heterocyclic carbine gold hydroxide complex: a golden sython †", Chem. Commun., 2010, vol. 46, pp. 2742-2744.
Gorin, David J., et al., "Ligand Effects in Homogeneous Au Catalysis", Chem. Rev., 2008, vol. 108, pp. 3351-3378.
Hahn, F. Ekkehardt, et al., "Heterocyclic Carbenes: Synthesis and Coordination Chemistry", Angew. Chem. Int. Ed., 2008, vol. 47, pp. 3122-3172.
Han, Xiaoqing et al., "Gold(I)-Catalyzed Intramolecular Hydroamination of Alkenyl Carbamates", Angew. Chem. Int. Ed., 2006, vol. 45, pp. 1747-1749.
Hindi, Khadijah M., et al., "The Medicinal Applications of Imidazolium Carbene-Metal Complexes", Chem. Rev., 2009, vol. 109, pp. 3859-3884.
Jimenez-Nunez, Eloisa et al., "Gold-Catalyzed Cycloismerizations of Enzynes: A Mechanistic Perspective", Chem. Rev., 2008, vol. 108, pp. 3326-3350.
Kissner, Reinhard, et al., "The hydrolysis of gold(I) in aqueous acetonitrile solutions", J. Chem. Soc., Dalton Trans., 1997, pp. 1773-1777.

(Continued)

*Primary Examiner* — Joseph Kosack
(74) *Attorney, Agent, or Firm* — Christopher J. Knors; Moore & Van Allen PLLC

(57) ABSTRACT

Gold (I) hydroxide complexes of the form Z—Au—OH and digold complexes of the form Z—Au-(μOH)—Au—Z where groups Z are two electron donors are provided. The groups Z may be carbenes, for example nitrogen containing heterocyclic carbenes (NHCs), phosphines or phosphites. The complexes can be used as catalysts, for example in reactions such as hydration of nitriles, skeletal arrangement of enynes, alkoxycyclization of enynes, alkyne hydration, the Meyer-Shuster reaction, 3,3' rearrangement of allylic acetates, cyclization of propargylic acetates, Beckman rearrangements and hydroamination. The complexes can be used in medicine, for example in the treatment of cancer.

13 Claims, 2 Drawing Sheets

(56) References Cited

OTHER PUBLICATIONS

Li, Zigang et al., "Gold-Catalyzed Organic Transformations", Chem. Rev., 2008, vol. 108, pp. 3239-3265.
Marcon, Giordana et al., "Gold(III) Complexes with Bipyridyl Ligands: Solution Chemistry, Cytotoxicity, and DNA Binding Properties", J. Med. Chem., 2002, vol. 45, pp. 1672-1677.
Marion, Nicolas et al., "$Au^1$-Catalyzed Tandem [3,3] Rearrangement—Intramolecular Hydroarylation: Mild and Efficient Formation of Substituted Indenes", Angew. Chem. Int. Ed., 2006, vol. 45, pp. 3647-3650.
Marion, Nicolas et al., "[(NHC)$Au^1$]-Catalyzed Acid-Free Alkyne Hydration of Part-per-Million Catalyst Loadings", J. Am., Chem. Soc., 2009, vol. 131, pp. 448-449.
Marion, Nicolas et al., "[(NHC)$Au^1$]-Catalyzed Rearrangement of Allylic Acetates", Organic Letters, 2007, vol. 9, No. 14, pp. 2653-2656.
Marion, Nicolas et al., "[(NHC)$Au^1$]-Catalyzed Formation of Conjugated Enones and Enals: An Experimental and Computational Study", Chem. Eur. J., 2007, vol. 13, pp. 6437-6451.
Marion, Nicolas et al., "N-Heterocyclic carbenes in gold catalysis", Chem. Soc. Rev., 2008, vol. 37, pp. 1776-1782.
Mezailles, Nicolas et al., "Phosphine Gold(I) Bis-(trifluoromethanesulfony)imidate Complexes as New Highly Efficient and Air-Stable Catalysts for the Cycloisomerization of Enynes", Organic Letters, 2005, vol. 7, No. 19, pp. 4133-4136.
Mizushima, Eiichiro et al., "Highly Efficient $Au^1$-Catalyzed Hydration of Alkynes", Angew. Chem. Int. Ed., 2002, vol. 41, No. 23, pp. 4563-4565.
Molander, Gary A., et al., "Organotrifluoroborates and Monocoordinated Palladium Complexes as Catalysts—A Perfect Combination of Suzuki-Miyaura Coupling", Angew. Chem. Int. Ed., 2009, vol. 48, pp. 9240-9261.
Nieto-Oberhuber, Cristina et al., "Cationic Gold(I) Complexes: Highly Alkynophilic Catalysts for the exo-and endo- Cyclization of Enynes", Angew. Chem. Int. Ed., 2004, vol. 43, pp. 2402-2406.
Nun, Pierrick et al., "A combined mechanistic and computational study of the gold(I)-catalyzed formation of substituted indenes", Org. Biomol. Chem., 2011, vol. 9, pp. 101-104.
Partyka, David V., et al., "Relativistic Functional Groups: Aryl Carbon-Gold Bond Formation by Selective Transmetalation of Boronic Acids", Angew. Chem. Int. Ed., 2006, vol. 45, pp. 8188-8191.
Pyykko Pekka et al., "Theory of the $d^{10}$- $d^{10}$ Closed-Shell Attraction. 4. $X(AuL)_n^{m+}$Centered Systems", Organometallics, 1998, vol. 17, pp. 4842-4852.
Qiu, Yong-Qing et al., "Quantum Chemistry Calculation on Structures and NLO Cofficients of $H_3PAuR$ Type Mononucleus Au(1) Complex", Chemical Journal of Chinese Universities, 2006, vol. 27, No. 9, pp. 1703-1707.
Ramon, Ruben S., et al., "[{Au(IPr)}$_2$(μ-OH)]X Complexes: Synthetic, Structural and Catalytic Studies", Chem. Eur. J., 2011, vol. 17, pp. 1238-1246.
Ramon, Ruben S., et al., "Au/Ag-Cocatalyzed Aldoximes to Amides Rearrangement under Solvent- and Acid-Free Conditions", J. Org. Chem., 2009, vol. XXX, No. XX, XXXX.
Ramon, Ruben S., et al., "[(NHC)AuC1]-catalyzed Meyer-Schuster rearrangement: scope and limitations", Tetrahedron, 2009, vol. 65, pp. 1767-1773.
Raubenheimer, Helgard G., et al., "Carbene complexes of gold: preparation, medical application and bonding", Chem. Soc. Rev., 2008, vol. 37, pp. 1998-2011.
Ricard, Louis et al., "Synthesis and Reactivity of Air-Stable N-Heterocyclic Carbene Gold(I) Bis(trifluoromethanesulfonyl)imidate Complexes", Organometallics, 2007, vol. 26, pp. 4704-4707.
Roesky, Herbert W., et al., "Organometallic Hydroxides of Transition Elements", Chem. Rev., 2006, vol. 106, pp. 3813-3843.
Scott, Natalie M., et al., "Stabilization of Organometallic Species Achieved by the Use of N-Heterocyclic Carbene (NHC) Ligands", Eur. J. Chem., 2005, pp. 1815-1828.
Shen, Kuang et al., "What are the $pK_a$ values of C-H bonds in aromatic heterocyclic compounds in DMSO?", Tetrahedron, 2007, vol. 63, pp. 1568-1576.
Suzaki, Yuji et al., "Transmetalation of Phenylplatinum(II) Complex. Isolation and Characterization of a Dinuclear Intermediate in Intermolecular Phenyl Ligand Transfer", Organometallics, 2004, vol. 23, pp. 5081-5084.
Tsui, Emily Y., et al., "Reactions of a Stable Monomeric Gold(I) Hydride Complex", Angew. Chem. Int. Ed., 2008, vol. 47, pp. 8937-8940.
Yang, Yi., et al., "New Gold Clusters [$Au_8L_6$]($BF_4$)$_2$ and [$(AuL)_4$]($BF_4$)$_2$ (L=P(mesityl)$_3$)$^1$", J. Am. Chem. Soc., 1994, vol. 116, pp. 6983-6984.
Acevedo-Chavez, Rodolfo, et al., Transition metal compounds of the purinic isomer allopurinol Part 1, Transition Metal Chemistry 15(6), 434-438 (1990) and abstract.
Acevedo-Chavez, Rodolfo, et al., Antiferromagnetic coupling in the cyclic octanuclear compound [Cu(II) (micro-3,5-dimetnylpyrazolate)(micro-OH)] and its Analogue [Cu(II)(micro-pyrozolate)(micro-OH)], Journal of Solid State Chemistry 132, 24-32 (1997) and abstract.
Ainscough, Eric W., et al., The interaction of 1-methylimidazoline-2(3H)-thione with copper (II) salts, Journal the Chemical Society Dalton Transactions: Inorganic Chemistry, 1. 39-42 (1989) and abstract.
Aoki, Massao. et al., Bidentate amidine ligands for nickel(0)-mediated coupling of carbon dioxide with unsaturated coupling hydrocarbon, Chem. Commun. 2568-2569 (2004).
Aresta, Michele, Carbon Dioxide Recovery and Utilization, Kluwer Academic Publishers. Dordrecht, The Netherlands. 210-277, 394-402 (2003).
Bonet, Amadeu, et al., The selective catalytic formation of beta-boryl aldehydes through a base-free approach, Org. Biomol. Chem., 7, 1533-1535 (2009).
Boogaerts, Ine I.F., et al., Carboxylation of C-H Bonds Using N-Heterocyclic Carbene Gold(I) Complexes, J. Am. Chem. Soc., 132. 8858-8859 (2010).
Boogaerts, Ine I.F., et al., Carboxylation of N-H/C-H Bonds Using N-Heterocyclic Carbene Copper(I) Complexes, Angew Chem 122. 8856-8859 (2010).
De Fremont, Pierre, et al., Synthesis of Well-Defined N-Heterocyclic Carbene Silver(I) Complexes, Organometallics, 24, 6301-6309 (2005).
Demember, John R., et al., Silver(I) Chemistry in Aqueous Alkaline Media, 2. Study of the Interaction of Silver(I) with beta-Disulfone Carbanions in Aqueous Alkaline Media, J. Am. Chem. Soc., 105(17) 5647-5652 (1963) and abstract.
Dupuy, Stephanie, et al., Decarboxylation of aromatic carboxylic acids by gold(I)-N-heterocyclic carbine (NHC) complexes, Chem. Commun. 47, 5455-5457 (2011).
Fortman, George C., et al., A Versatile Cuprous SynthonlCu(IPr)(OH)](1Pr=1,3 bis(diisopropylphenyl) imidazol-2-ylidene), Organometallics, 29, 2966-3972 (2010).
Franks, Russell J., et al., Palladium-Catalyzed Carboxylative Coupling of Allylstannanes and Ally! Halides, Organometallics, 19, 1458-1460 (2000).
Gaillard, Sylvain, et al., A N-heterocyclic carbene gold hydroxide complex: a golden synthon, Chem. Commun., 46, 2742-2744 (2010).
Hamashima, Yoshitaka, et al., Catalytic Enantioselective Fluorination of Oxindoles, J. Am. Chem. Soc., 127. 10164-10165 (2005).
Jessop, Philip G., et al., Recent advances in the homogeneous hydrogenation of carbon dioxide, Coordination Chemistry Reviews, 248, 2425-2442 (2004).
Johansson, Roger, et al., Insertion of CO2 into a palladium allyl bond and a Pd(II) catalysed carboxylation of ally! stannanes, Dalton Trans., 488-492 (2007).
Jurkauskas, Valdas, et al, Conjugate Reductionof alpha,beta-Unsaturated Carbonyl Compounds Catalyzed by a Copper Carbene Complex, Organic Letters, 5(14), 2417-2420 (2003).
Kaur, Harneet, et al, (NHC)CU(NHC=N-Heterocyclic Carbene) Complexes as Efficient Catalysts for the Reduction of Carbonyl Compounds. Organometallics, 23, 1157-1160 (2004).

(56) References Cited

OTHER PUBLICATIONS

Kissner, Reinhard, et al., The Hydrolysis of gold(I) in aqueous acetonitrile solutions. J. Chem. Soc., Dalton Trans., 1773-1777 (1997) and abstract.
Mankad, Neal P., et al, Synthesis, Structure, and CO2 Reactivity of a Two-Coordinate (Carbene)copper(I) Methyl Complex, Organometallics, 23. 1191-1193 (2004) and abstract.
Marion, Nicolas, et al, [(NHC)Au]-Catalyzed Formation of Conjugated Enones and Enals: An Experimental and Computational Study, Chem., Eur. J., 13, 6437-6451 (2007).
Muthu, Sebastian, et al., Coordination network of Ag(I) and N,N'-bis(3-pyridine-carboxamide)-1,6-hexane: structures and anion exchange, J. Chem. Soc., Dalton Trans., 4561-4568 (2002).
Nemoto, Koji, et al., Carboxylation of indoles pyrroles with CO2 in the presence of dialkylaluminum halides, Tetrahedron Letters 50, 4512-4514 (2009).
Olah, George A., et al., Efficient Chemoselective Carboxylation of Aromatics to Arylcarboxylic Acids with a Superelectrophilically Activated Carbon Dioxide—Al2Cl5/Al System, J. Am. Chem. Soc., 124, 11379-11391 (2002).
Papai, Imre, et al., Mechanistic Details of Nickel(0)-Assisted Oxidative Coupling CO2 with C2H4, Organometallics. 23, 5252-5259 (2004)>.
Park, Chul Min, et al., Synthesis and structure-activity relationship of 1H-indole-3-carboxylic acid pyridine-3-ylamides: A novel series of 5-HT2c receptor antagonists, Bioorganic & Medicinal Chemistry Letters, 3844-3847 (2008).
Pyykkoe, Pekka, et al, Theory of the d10-d10 Closed-Shell Attraction 4. X(AuL)nm+ Centered Systems, Organometallics, 17, 4842-4852 (1998) and abstract.
Qiu, Yong-Qing, et al., Quantum chemistry calculation on structures and NLO coefficients of H3PauR type mononucleaus Au(I) complex, Inst. Functional Meter. Chem. Fac. Chem., Northeast Normal Univ., Gaodeng Xuexiao Huaxue Xuebao,27(9), 1703-1707 (2006).
Rajeswaran, Walajapet G., et al., Studies on Protection of Oxindoles, Tetrahedron, 54, 11375-11380 (1998).
Saito, Shinichi, et al., Nickel-Mediated Regio- and Chemoselective Carboxylation Alkynes in the Presence of Carbon Dioxide, J. Org. Chem. 64, 3975-3978 (1999).
Sakakura, Toshiyasu, et al., Transformation of Carbon Dioxide, Chem. Rev., 107, 2365-2387 (2007).
Takimoto, Masanori, et al., Highly Enantioselective Catalytic Carbon Dioxide Incorporation Reaction: Nickel-Catalyzed Asymmetric Carboxylative Cyclization of Bis-1,3-dienes, J. Am. Chem. Soc., 126, 5956-5957 (2004).
Ukai, Kazutoshi, et al., Rhodium(I)-Catalyzed Carboxylation of Aryl- and Alkenylboronic Esters with CO2, J. Am. Chem Soc., 128, 8706-8707 (2006).
Yeung, Charles S., et al., Beyond Aresta's Complex: Ni- and Pd-Catalyzed Organozinc Coupling with CO2, J. Am. Chem. Soc., 130, 7826-7827 (2008).
European Patentoffice, PCT International Search Report and Written Opinion of the International Searching Authority for International ApplicationNo. PCT/GB2011/000868 date of completion Aug. 9, 2011.
GB Intellecutal Property Office, GB Search Report for GB Application No. GB1009656.8 dated Oct. 11, 2010.
North, Michael, Synthesis of beta,gamma-Unsaturated Acids from Allenes and Carbon Dioxide, Angew. Chem. Int. Ed., 48, 4104-4105 (2009).
Correa, Arkaitz, et al., Palladium-Catalyzed Direct Carboxylation of Aryl Bromides with Carbon Dioxide, J. Am. Chem. Soc., 131, 15974-15975 (2009).
U.S. Patent and Trademark Office, U.S. Appl. No. 13/702,886, Non-Final Office Action dated Oct. 9, 2014, 16 pages.
Chinese Patent Office, Chinese application No. 2011800119551. Office Action dated Dec. 26, 2013, 7 pages.
Japanese Patent Office, Japanese Application No. 2012-555480. Office Action dated Nov. 11, 2014, 5 pages.
Citadelle et al., "Simple and Versatile Synthesis of Copper and Silver N-Heterocyclic Carbene Complexes in Water or Organic Solvents," The Royal Society of Chemistry 2010, Apr. 19, 2010, Dalton Trans., 2010,39, pp. 4489-4491.

* cited by examiner

Table 4

| Entry | Gold catalyst | HBF$_4$ (eq.) | A<br>Nitrile hydration | B<br>Skeletal rearrangement | C<br>Alkoxy cyclisation | D<br>Alkyne hydration | E<br>Meyer Schuster | F<br>3,3' rearrangement | G<br>Propargylic acetate | H<br>Beckman type rearrangement[b] | I<br>Hydro amination |
|---|---|---|---|---|---|---|---|---|---|---|---|
| 1 | - | 1 | - | <2% | - | - | | <5% | | - (48%) | - |
| 2 | AuOH | - | 23% | - | 16% | 12% | | - | | 17% (5%) | - |
| 3 | AuOH | 0.5 | 99% | - | 90% | 90% | | - | | 46% (5%) | - |
| 4 | AuOH | 1 | 98% | >99% | 90% | >99% (93%)[a] | | 85% | | 81% (4%) | >99% |
| 5 | AuOH | 1.5 | - | >99% | >99% | >99% | 100% | >99% (93%)[a] | 100% | 92% (4%) | >99% |
| 6 | Au$_2$(μOH) | - | >99% | 38% | 30% | 88% | | - | | 25% (6%) | - |
| 7 | Au$_2$(μOH) | 1 | - | >99% | >99% | >99% | | >99% | | 90% (6%) | >99% |

[a] isolated yield, [b] conversion into amide and by products in brackets

Fig. 3

GOLD COMPLEXES

The work leading to this invention has received funding from the European Research Council under the European Community's Seventh Framework Programme (FP7/2007-2013)/ERC grant agreement no 227817.

FIELD OF THE INVENTION

The present invention related to the provision of gold hydroxide complexes, their manufacture and their uses.

BACKGROUND TO THE INVENTION

Late transition metal (LTM) hydroxide complexes have been described as environmentally friendly complexes that can act as versatile synthetic reagents. (Reference 1) Such synthons have permitted the isolation of a large number of products through simple environmentally benign reaction chemistry. Amongst the LTM, no examples of mononuclear linear copper and silver hydroxide appear to have been reported and only three examples are known for gold; these all involve gold (III) metal centres. (1-2). Gold (I) is of interest as it finds increasing use in organometallic chemistry, homogeneous catalysis (3) and medicine (4).

DESCRIPTION OF THE INVENTION

According to a first aspect the present invention provides a gold (I) hydroxide complex of the form Z—Au—OH wherein the group Z is a two-electron donor ligand.

The two-electron donor ligand may be, for example a phosphine, a carbene or a phosphite ligand.

Examples of phosphine ligands include those of the form $R_3P$ wherein each R group may be the same or different and may be alkyl, aryl, cyclic or heterocyclic. All of these groups may be substituted or unsubstituted, saturated or unsaturated. Where the group R is cyclic or heterocyclic it may be aromatic.

Advantageously the phosphine ligand may be triphenylphosphine or substituted triphenylphenylphosphine. For example: tris(2-tolyl)phosphine and tris(2-MeO-phenyl)phosphine and tris(2,4-di-tert-butylphenyl) phosphine.

Examples of phosphite ligands include those of the form $RO_3P$ wherein each RO group may be the same or different and R may be alkyl, aryl, cyclic or heterocyclic. All of these groups may be substituted or unsubstituted, saturated or unsaturated. Where the group R is cyclic or heterocyclic it may be aromatic.

Advantageously the phosphite groups may be triphenylphosphite or substituted triphenyl phosphite, typically bearing sterically demanding substituents, for example: tris(2-tolyl)phosphite and tris(2-MeO-phenyl)phosphite and tris(2,4-di-tert-butylphenyl) phosphite.

Examples of carbene ligands include cyclic or acyclic carbenes having one or more heteroatoms. The heteroatom (or heteroatoms) may be the same or different and may be N, O or S for example. The presence of such heteroatoms stabilises the carbene ligand.

Advantageously a carbene ligand is a heterocyclic carbene ligand, especially a nitrogen containing heterocyclic carbene ligand (NHC). The NHC may have a five or six membered ring, typically a five membered ring. N-heterocyclic carbene ligands (NHC ligands) have been shown to provide good stabilising effects for reactive intermediates and their use in organometallic chemistry, catalysis and medicine is increasing (5,6).

The NHC employed in the gold hydroxide complexes may be saturated or unsaturated and may contain one or more nitrogen atoms an optionally may contain other heteroatoms (such as O and S) in the ring.

For example the ligand may have the form

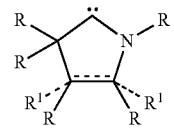

wherein the groups R may be the same or different, the groups $R^1$ where present may be the same or different and the dashed line in the ring represents optional unsaturation. One or more of the carbon atoms in the ring (apart from the carbene carbon) may be substituted with O or S. Each R and $R^1$ may be, independently for each occurrence, selected from: H, a primary or secondary alkyl group (for example C1-C10 or even C1-C4) that may be substituted or unsubstituted, substituted or unsubstituted phenyl, substituted or unsubstituted naphthyl, or substituted or unsubstituted anthracenyl, or a functional group selected from the group consisting of halo, hydroxyl, sulfhydryl, cyano, cyanato, thiocyanato, amino, nitro, nitroso, sulfo, sulfonato, boryl, borono, phosphono, phosphonato, phosphinato, phospho, phosphino, and silyloxy;

Advantageously NHC ligands bearing two nitrogen atoms in the ring, each adjacent the carbene carbon may be employed. The NHC carbene ligands of this type may have the form:

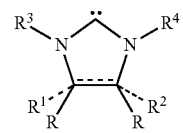

wherein each of the groups R, $R^1$ $R^2$, $R^3$ and $R^4$ may be the same or different and the dashed line in the ring represents optional unsaturation, wherein $R^1$ and $R^2$ are absent. Each R and $R^1$, $R^2$, $R^3$ and $R^4$ may be, independently for each occurrence, selected from: H, a primary or secondary alkyl group (for example C1-C10 or even C1-C4) that may be substituted or unsubstituted, substituted or unsubstituted phenyl, substituted or unsubstituted naphthyl, or substituted or unsubstituted anthracenyl, or a functional group selected from the group consisting of halo, hydroxyl, sulfhydryl, cyano, cyanato, thiocyanato, amino, nitro, nitroso, sulfo, sulfonato, boryl, borono, phosphono, phosphonato, phosphinato, phospho, phosphino, and silyloxy;

Advantageously the groups $R^3$ and $R^4$ may be substituted or unsubstituted aromatic rings that may be heterocyclic aromatic rings. Substituents R, $R^1$ $R^2$, $R^3$ and $R^4$ in the structures above may include alkyl and unsaturated alkyl groups, aryl groups that may be substituted and may contain heteroatoms.

Suitable examples of NHC carbene ligands include those according to formulas I to IV below:

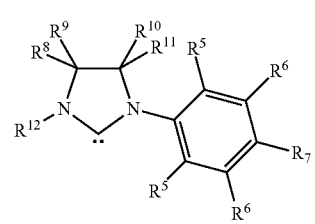

I

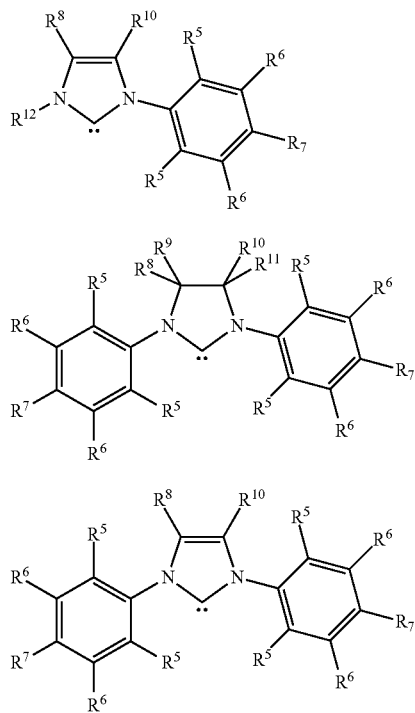

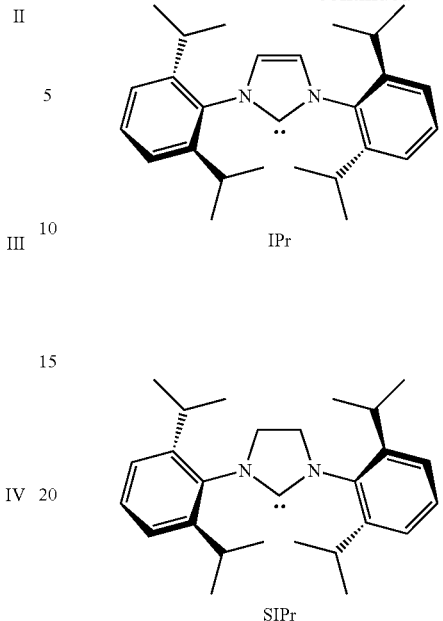

IPr

SIPr

Wherein each group $R^5$, $R^6$ and $R^7$, is independently for each occurrence selected from: H, a primary or secondary alkyl group (for example C1-C10 or even C1-C4) that may be substituted or unsubstituted, substituted or unsubstituted phenyl, substituted or unsubstituted naphtyl, or substituted or unsubstituted anthracenyl, or a functional group selected from the group consisting of halo, hydroxyl, sulfhydryl, cyano, cyanato, thiocyanato, amino, nitro, nitroso, sulfo, sulfonato, boryl, borono, phosphono, phosphonato, phosphinato, phospho, phosphino, and silyloxy; $R^8$, $R^9$, $R^{10}$ and $R^{11}$ are each independently for each occurence H, a substituted or unsubstituted alkyl group (for example C1-C10 or even C1-C4), substituted or unsubstituted aryl, or in formulas (II) and (IV) together with the carbons carrying them form a substituted or unsubstituted, fused 4-8 membered carbocylic ring or a substituted or unsubstituted, fused aromatic ring, preferably a fused phenyl ring; and $R^{12}$ is alkyl (for example C1-C10 or even C1-C4) or a cycloalkyl (for example C3-C8).

For example these NHC carbenes:

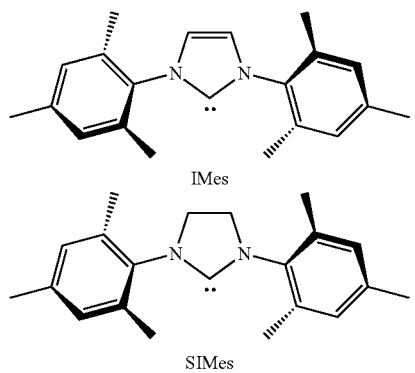

are suitable examples of the NHC carbene family for the formation of the gold hydroxide complexes, the alkyl substituted aromatic rings providing additional stabilisation to the carbene lone pair of electrons.

Complexes of the form NHC—Au—OH (i.e. where Z is an NHC) have been postulated as potential intermediates in catalytic systems involving the use of gold complexes such as NHC—Au—CL in combination with $AgSbF_6$ (27). However no direct evidence of the actual existence of such species has previously been provided. The methods of the present invention as discussed hereafter provide NHC—Au—OH complexes that can be isolated in the solid form with a good level of purity (typically >97%). Similarly, the existence of a complex of the form Z—Au—OH, where Z is acetonitrile ($CH_3CN$) has been suggested as one of the possible intermediates in a reaction mixture (29) but not confirmed. Thus the present invention provides solid products comprising, consisting of, or consisting essentially of a complex of the form Z—Au—OH, in particular where Z is an NHC. The Z—Au—OH complexes can find use as catalysts as described hereafter. For several reactions the use of silver compounds as part of the catalytic system, as found with prior art gold catalysts, is not required.

The gold (I) hydroxide complex may be made for example by displacement of a halogen, for example chloride from a gold complex of the form Z—Au—X, where X is halogen. The Z—Au—X complexes may be made by any route such as is known in the art.

For example where Z is an NHC ligand and X is Cl gold halogen complexes may be synthesised by mixing (L)AuCl (L=dimethylsulfide or tetrahydrothiophene ligand) and an NHC in a solvent to lead to (NHC)AuCl complexes as described in "Synthesis and Structural Characterization of N-Heterocyclic Carbene Gold(I) Complexes." de Fremont, P.; Scott, N. M.; Stevens, E. D.; Nolan, S. P. Organometallics, 2005, 24, 2411-24. Alternatively, the (NHC)AuCl can be made from HAuCl$_4$ and the NHC.HX salt in the presence of a base.

For example a gold (I) hydroxide complex may be made by the reaction of a gold (I) halide complex with an hydroxide, for example an alkali metal hydroxide as shown in scheme 1 below and described more fully hereafter in examples of the synthetic method.

Scheme 1

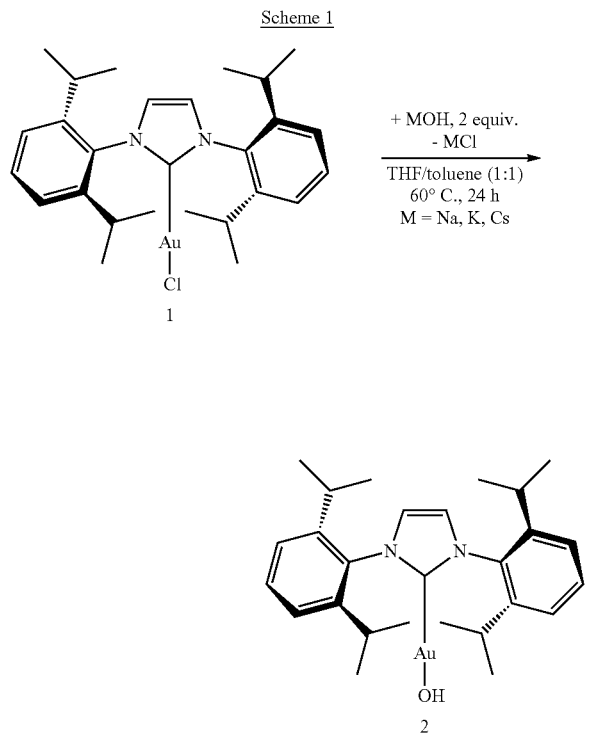

Compound 1 above is the commercially available [AuCl(IPr)] (12) (where IPr=N,N'-bis(2,6-diisopropylphenyl)imidazol-2-ylidene)).

This reaction has been shown to proceed in good yields in air even with only technical grade solvents. Thus according to a second aspect the present invention provides a method of manufacture of a gold (I) complex according to the first aspect of the invention comprising: reacting a gold (I) halide complex of the form Z—Au—X, wherein Z is a two-electron donor ligand as described before and X is halogen; with an alkali metal hydroxide. Typical solvents in which the reaction may be carried out include halogenated solvents. For example chlorinated solvents such as dichloromethane or dichloroethane. Ethereal solvents such as THF or mixtures of ethereal solvents may also be employed, with or without the presence of aromatic hydrocarbons. Mixtures of aromatic hydrocarbons with oxygenated solvents such as ethereal solvents, for example THF/toluene mixtures, for example a 1:1 THF/toluene mixture may be employed.

The product gold hydroxide complex may be isolated by evaporation of the solvent, which may be followed by washing with a hydrocarbon, such as toluene and filtration and or drying to remove the last of the solvents employed. Alternative isolation procedures include firstly carrying out the reaction in a solvent which dissolves the product e.g. THF. A liquid in which the product is not so soluble is then added (e.g. toluene) and distillation is carried out to remove some or all of the solvent, thereby precipitating or crystallising out the product. Simple filtration and drying produces the isolated gold hydroxide product.

The gold (I) hydroxide complexes of the invention can find use as catalysts or in medicine (for example as anticancer agents) and as synthons. The gold (I) hydroxide complexes of the invention can find use as synthetic intermediates for the production of a wide range of gold complexes that may themselves find use as catalysts or in medicine. The gold (I) hydroxide complexes of the invention may be used as a catalyst, or for the in situ production of a catalyst, for carrying out many transformations. For example a transformation selected from the group consisting of: hydration of nitriles, skeletal arrangement of enynes, alkoxycyclisation of enynes, alkyne hydration, the Meyer-Shuster reaction, 3,3' rearrangement of allylic acetates, cyclisation of propargylic acetates, Beckman rearrangements and hydroamination.

Examples of the synthetic utility of the exemplary complex 2 are shown in Scheme 2 below.

Scheme 2

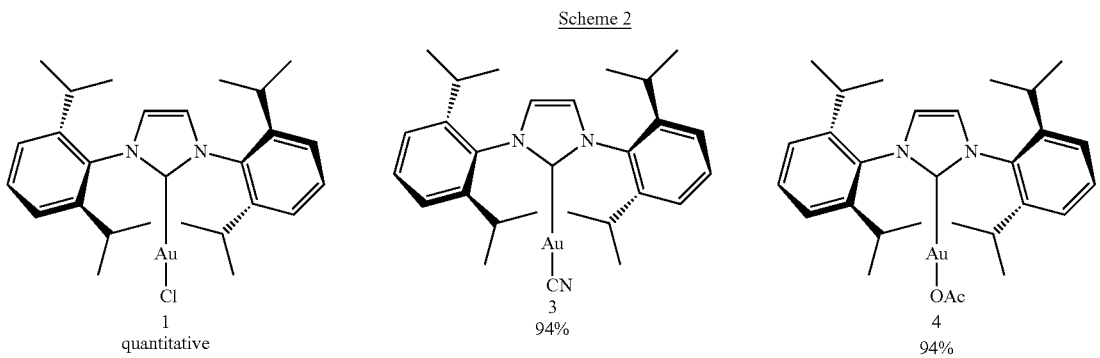

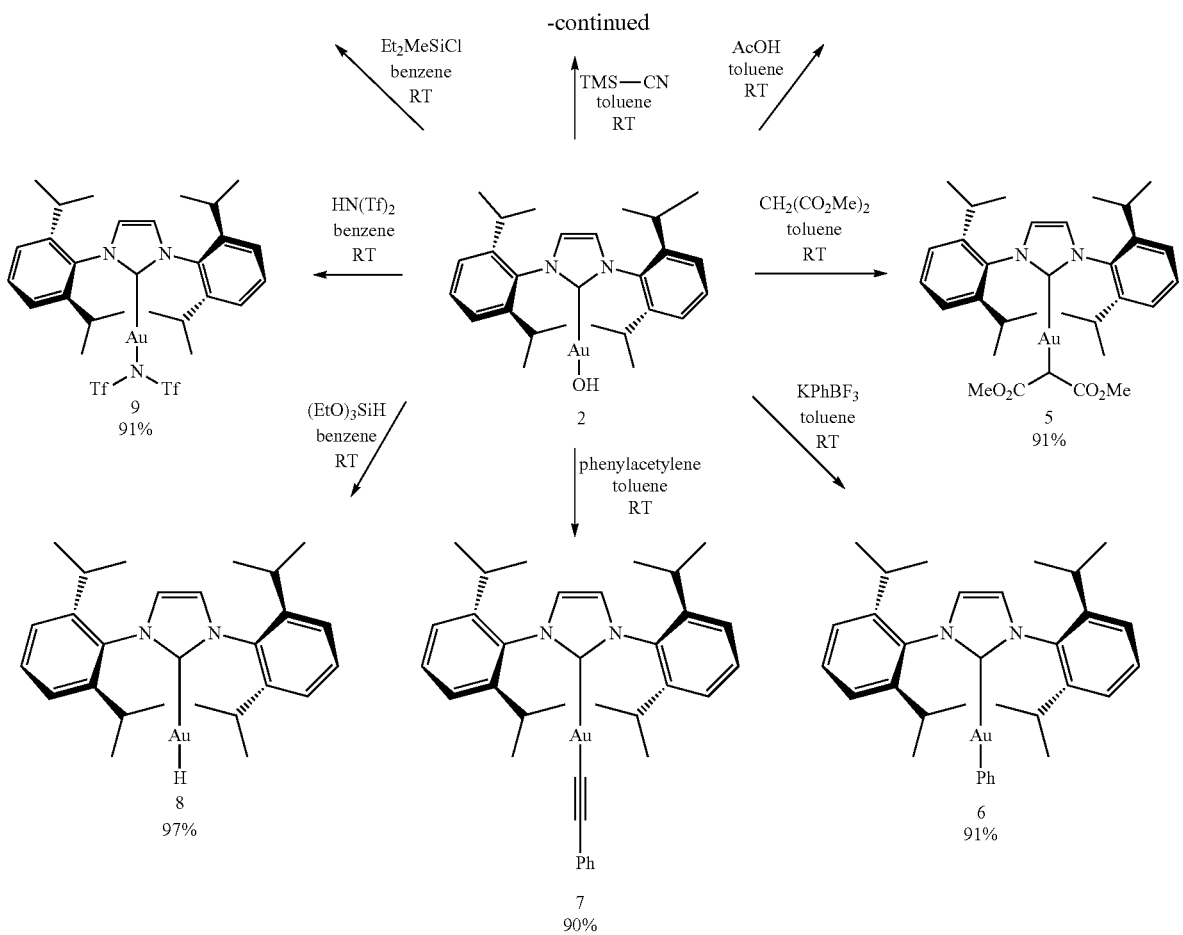

Thus it can be seen that the hydroxide group on a complex of the invention can be readily replaced with a wide range of substituents often in high yield, often due to its basic nature. The use of hydroxide complexes such as 2 can be advantageous in comparison with alternative routes. Reactions may generally be carried out in air and there is often no need to use auxiliary reagents as can be required with other synthetic pathways.

For example Gray and co-workers have recently shown a congener of 1 to be an efficient synthetic precursor to generate gold-aryl bonds. (7) This reaction involved the use of a base and a boronic acid in the synthesis of complex 6 shown in the scheme above. As complexes such as 2 have the base function already on board, they can directly react with boronic acids. Indeed a reaction performed at room temperature with 2 to make 6 as indicated in the scheme above proved quantitative. Furthermore other boron-based delivery agents, the trifluoroboronates developed by Molander, (8) can also perform the task in high yields. In this manner, [Au(Ph)(IPr)] 6 was obtained with 91% isolated yield in toluene in 6 h at room temperature. Thus reactions of the gold (I) hydroxide complexes of the invention with boron reagents leading to Au—C bond formation can permit the preparation of a large number of gold complexes carrying different functional groups by using the one step synthetic route illustrated in Scheme 1.

Other acid proton (pKa<ca. 30) containing reagents may be employed as possible reaction partners and lead to neutral species or anion-cation pairs (for example [NHC—Au—Y]$^+$ X$^-$ where Y=Phosphine, phosphite, NHC and X is a suitable counterion).

The synthesis of gold acetylides usually involves bases and heating when alkali metal hydroxides are used or cooling if lithium bases are employed. However [Au(CCPh)(IPr)] (7) was obtained in 90% yield when 2 was reacted with phenyl acetylene in toluene at room temperature.

The most fundamental protonolysis reaction would be one that delivers H to gold. Tsui and co-workers have recently achieved such a delivery from [Au(O$^t$Bu)(IPr)]. (9) Using a similar protocol, the H atom can be successfully delivered using 2 as a synthon and a silane as a H source. This route leads to the formation of [Au(H)(IPr)] (8) in 97% yield. This result suggests that the formation of the Si—O bond as a driving force in reactions involving 2 may be quite general and amenable to a large variety of silicon-based reagents.

Of the many versions of gold-centered catalysts one that has attracted significant attention is the so-called Gagosz-type complex [Au(NTf$_2$)(IPr)] 9 (NTf$_2$=bis-(trifluoromethanesulfonyl)imidate). (10) This compound is a single component catalyst not requiring the usual activation performed by a silver-based co-catalyst for other gold-based catalysts. Complex 9 was previously accessible by reaction of 1 with the light- and moisture-sensitive and costly AgNTf$_2$. The isolation of 2 permits the straightforward synthesis of 9 by protonolysis with HNTf$_2$ at room temperature in a 91% yield. Thus an improved synthetic route to 9 is provided and constitutes a third aspect of the present invention.

The gold (I) hydroxide complexes of the invention are basic and can be used to remove protons from a wide variety of sources. For example fluorinated organic compounds as discussed in the Examples section hereafter.

A yet further use of the gold (I) hydroxide complexes of the present invention is in the preparation of dinuclear gold complexes which themselves can be versatile catalysts.

Thus according to a yet further aspect the present invention provides a digold hydroxide complex according to general formula V:

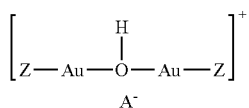
(V)

wherein each Z is a two-electron donor ligand that may be the same or different and $A^-$ is an anion.

The two-electron donor ligands Z may be of the same types discussed above with respect to the gold (I) complexes of the first aspect of the invention. A complex of formula V where the anion A is $BF_4^-$, both groups Z are $PR_3$ and each R is mesityl is known (ref 28) and has been described as an intermediate in the synthesis of certain gold cluster complexes, but not for use as a catalyst. Thus the present invention provides complexes of formula V with the proviso that when A is $BF_4^-$, both Z groups are the same and are phosphines of the form $PR_3$, each group R is not mesityl.

The anion $A^-$ for complexes of formula V may be for example $BF_4^-$, $PF_6^-$, $SbF_6^-$, $BAr_{f4}^-$ ($=[B\{C_6H_3(CF_3)_2\}_4]^-$) or FABA ($=[B(C_6F_5)_4]^-$).

The digold complexes of formula V can be prepared from the gold (I) hydroxide complex of the form Z—Au—OH by reaction with a suitable acid HA in accordance with the following:

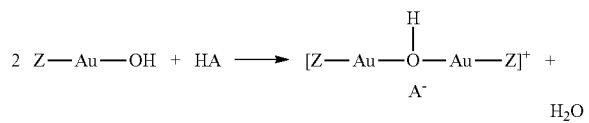

If different groups Z are required then, for example, two Z—Au—OH complexes having different groups Z may be used:

Thus according to a yet further aspect the present invention provides a method of manufacture of a gold complex of general formula V comprising: reacting a gold (I) complex according to the first aspect of the invention with an acid.

Formally the complexes of general formula V may be considered to comprise a gold complex according to the first aspect of the invention (Z—Au—OH) together with a salt of the form $Z-Au^+A^-$, however the exemplary compound has been shown to have gold atoms that are equivalent to each other by NMR data and X-ray structure determination. The hydroxide moiety forms a bridge between them. The complexes of general formula V can find use as catalysts, in synthesis and in medicine (for example as anti-cancer agents).

For use in catalysis the dinuclear gold complexes can be prepared as isolated materials that can be obtained in good purity (typically >97%). Thus the present invention provides solid products comprising, consisting of, or consisting essentially of a complex of the form of formula V, in particular where Z is an NHC. The complexes of formula V can find use as catalysts as described hereafter. For several reactions the use of silver compounds as part of the catalytic system, as found with prior art gold catalysts, is not required.

However in some circumstances they may be conveniently prepared in situ.

For example complex 2

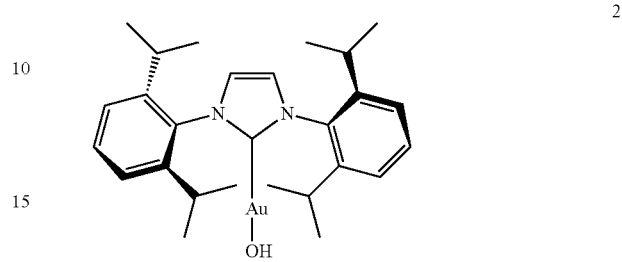

discussed above can be reacted with tetrafluoroboric acid diethyl ether complex in benzene to produce a 90% isolated yield of 12 below:

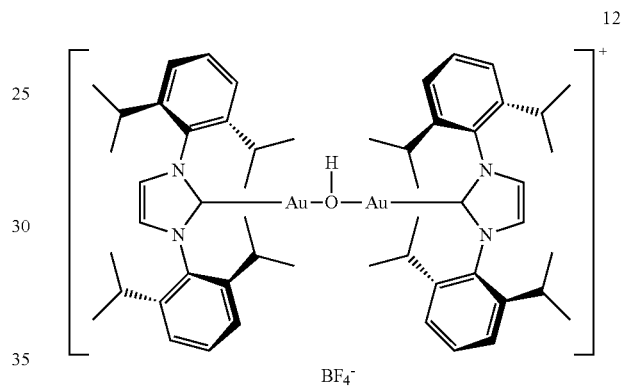

The complex 12 $[Au(IPr)]_2(\mu\text{-OH})BF_4$ is a versatile catalyst.

As an alternative to its preparation as an isolated material, 12 may be prepared for use as a catalyst in situ by providing Au(IPr)(OH) and $HBF_4 \cdot OEt_2$ (or $HBF_4$ in water) in a reaction mixture as discussed hereafter with reference to specific examples. Thus the gold (1) hydroxide complexes of the invention can be activated in situ for use as dinuclear gold hydroxide complexes by the use of a suitable acid.

Alternative methods of preparation of the dinuclear gold hydroxide complexes are available. for example complex 2 [Au(IPr)(OH)] may be converted to complex 12 $[Au(IPr)]_2(\mu\text{-OH})BF_4$ via an intermediate complex 13 $[Au(IPr)(CH_3CN)]BF_4$ which is converted to 12 by simply reacting with water.

The above interconversions are illustrated in Scheme 3 below.

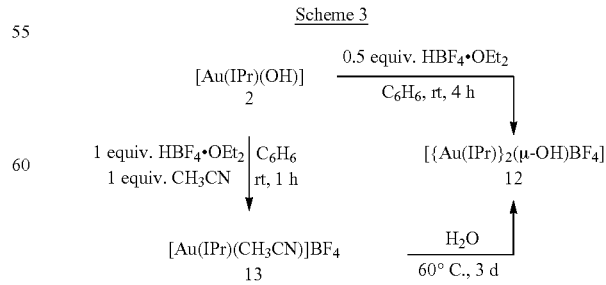

Scheme 3: Synthetic routes to $[Au(IPr)(CH_3CN)]BF_4$ 13 and $[\{Au(IPr)\}_2(OH)]BF_4$ 12.

Like the gold (I) hydroxide complexes of the invention the dinuclear (digold) complexes can find use as catalysts or in medicine (for example as anti-cancer agents) and as synthons.

Like the gold (I) hydroxide complexes of the first aspect of the invention the digold complexes of the invention may be used as a catalyst for carrying out many transformations. For example a transformation selected from the group consisting of: hydration of nitriles, skeletal arrangement of enynes, alkoxycyclisation of enynes, alkyne hydration, the Meyer-Shuster reaction, 3,3' rearrangement of allylic acetates, cyclisation of propargylic acetates, Beckman rearrangements and hydroamination.

For medical uses according to the present invention the gold (I) hydroxide complexes or digold complexes of formula V described above or a physiologically acceptable salt, ester or other physiologically functional derivative thereof may be used in methods of treatment. The method may comprise administering to a human or animal subject a therapeutically effective amount of a complex sufficient to ameliorate, treat or provide prophylaxis for the condition to be treated. For example the complexes may be used in the treatment of cancer.

For medical uses according to the present invention, the gold (I) hydroxide complexes or dinuclear (digold) complexes described above or a physiologically acceptable salt, ester or other physiologically functional derivative thereof may be presented as a pharmaceutical formulation, comprising the complex or physiologically acceptable salt, ester or other physiologically functional derivative thereof, together with one or more pharmaceutically acceptable carriers therefore and optionally other therapeutic and/or prophylactic ingredients. The carrier(s) must be acceptable in the sense of being compatible with the other ingredients of the formulation and not deleterious to the recipient thereof.

Pharmaceutical formulations include those suitable for oral, topical (including dermal, buccal and sublingual), rectal or parenteral (including subcutaneous, intradermal, intramuscular and intravenous), nasal and pulmonary administration e.g., by inhalation. The formulation may, where appropriate, be conveniently presented in discrete dosage units and may be prepared by any of the methods well known in the art of pharmacy. All methods include the step of bringing into association an active complex with liquid carriers or finely divided solid carriers or both and then, if necessary, shaping the product into the desired formulation.

Pharmaceutical formulations suitable for oral administration wherein the carrier is a solid are most preferably presented as unit dose formulations such as boluses, capsules or tablets each containing a predetermined amount of active complex. A tablet may be made by compression or moulding, optionally with one or more accessory ingredients. Compressed tablets may be prepared by compressing in a suitable machine an active complex in a free-flowing form such as a powder or granules optionally mixed with a binder, lubricant, inert diluent, lubricating agent, surface-active agent or dispersing agent. Moulded tablets may be made by moulding an active complex with an inert liquid diluent. Tablets may be optionally coated and, if uncoated, may optionally be scored. Capsules may be prepared by filling an active complex, either alone or in admixture with one or more accessory ingredients, into the capsule shells and then sealing them in the usual manner. Cachets are analogous to capsules wherein an active complex together with any accessory ingredient(s) is sealed in a rice paper envelope. An active complex may also be formulated as dispersable granules, which may for example be suspended in water before administration, or sprinkled on food. The granules may be packaged, e.g., in a sachet. Formulations suitable for oral administration wherein the carrier is a liquid may be presented as a solution or a suspension in an aqueous or non-aqueous liquid, or as an oil-in-water liquid emulsion.

Formulations for oral administration include controlled release dosage forms, e.g., tablets wherein an active complex is formulated in an appropriate release—controlling matrix, or is coated with a suitable release—controlling film. Such formulations may be particularly convenient for prophylactic use.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of an active complex with the softened or melted carrier(s) followed by chilling and shaping in moulds.

Pharmaceutical formulations suitable for parenteral administration include sterile solutions or suspensions of an active complex in aqueous or oleaginous vehicles.

Injectable preparations may be adapted for bolus injection or continuous infusion. Such preparations are conveniently presented in unit dose or multi-dose containers which are sealed after introduction of the formulation until required for use. Alternatively, an active complex may be in powder form which is constituted with a suitable vehicle, such as sterile, pyrogen-free water, before use.

An active complex may also be formulated as long-acting depot preparations, which may be administered by intramuscular injection or by implantation, e.g., subcutaneously or intramuscularly. Depot preparations may include, for example, suitable polymeric or hydrophobic materials, or ion-exchange resins. Such long-acting formulations are particularly convenient for prophylactic use.

Formulations suitable for pulmonary administration via the buccal cavity are presented such that particles containing an active complex and desirably having a diameter in the range of 0.5 to 7 microns are delivered in the bronchial tree of the recipient.

As one possibility such formulations are in the form of finely comminuted powders which may conveniently be presented either in a pierceable capsule, suitably of, for example, gelatin, for use in an inhalation device, or alternatively as a self-propelling formulation comprising an active complex, a suitable liquid or gaseous propellant and optionally other ingredients such as a surfactant and/or a solid diluent. Suitable liquid propellants include propane and the chlorofluorocarbons, and suitable gaseous propellants include carbon dioxide. Self-propelling formulations may also be employed wherein an active complex is dispensed in the form of droplets of solution or suspension.

Such self-propelling formulations are analogous to those known in the art and may be prepared by established procedures. Suitably they are presented in a container provided with either a manually-operable or automatically functioning valve having the desired spray characteristics; advantageously the valve is of a metered type delivering a fixed volume, for example, 25 to 100 microliters, upon each operation thereof.

As a further possibility an active complex may be in the form of a solution or suspension for use in an atomizer or nebuliser whereby an accelerated airstream or ultrasonic agitation is employed to produce a fine droplet mist for inhalation.

Formulations suitable for nasal administration include preparations generally similar to those described above for pulmonary administration. When dispensed such formulations should desirably have a particle diameter in the range 10 to 200 microns to enable retention in the nasal cavity; this may be achieved by, as appropriate, use of a powder of a suitable particle size or choice of an appropriate valve. Other suitable formulations include coarse powders having a particle diameter in the range 20 to 500 microns, for administration by rapid inhalation through the nasal passage from a container held close up to the nose, and nasal drops comprising 0.2 to 5% w/v of an active complex in aqueous or oily solution or suspension.

It should be understood that in addition to the aforementioned carrier ingredients the pharmaceutical formulations described above may include, an appropriate one or more additional carrier ingredients such as diluents, buffers, flavouring agents, binders, surface active agents, thickeners, lubricants, preservatives (including anti-oxidants) and the like, and substances included for the purpose of rendering the formulation isotonic with the blood of the intended recipient.

Pharmaceutically acceptable carriers are well known to those skilled in the art and include, but are not limited to, 0.1 M and preferably 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Preservatives and other additives may also be present, such as, for example, antimicrobials, antioxidants, chelating agents, inert gases and the like.

Formulations suitable for topical formulation may be provided for example as gels, creams or ointments. Such preparations may be applied e.g. to a wound or ulcer either directly spread upon the surface of the wound or ulcer or carried on a suitable support such as a bandage, gauze, mesh or the like which may be applied to and over the area to be treated.

Liquid or powder formulations may also be provided which can be sprayed or sprinkled directly onto the site to be treated, e.g. a wound or ulcer. Alternatively, a carrier such as a bandage, gauze, mesh or the like can be sprayed or sprinkle with the formulation and then applied to the site to be treated.

Therapeutic formulations for veterinary use may conveniently be in either powder or liquid concentrate form. In accordance with standard veterinary formulation practice, conventional water soluble excipients, such as lactose or sucrose, may be incorporated in the powders to improve their physical properties. Thus particularly suitable powders of this invention comprise 50 to 100% w/w and preferably 60 to 80% w/w of the active ingredient(s) and 0 to 50% w/w and preferably 20 to 40% w/w of conventional veterinary excipients. These powders may either be added to animal feedstuffs, for example by way of an intermediate premix, or diluted in animal drinking water.

Liquid concentrates of this invention suitably contain the complex or a derivative or salt thereof and may optionally include a veterinarily acceptable water-miscible solvent, for example polyethylene glycol, propylene glycol, glycerol, glycerol formal or such a solvent mixed with up to 30% v/v of ethanol. The liquid concentrates may be administered to the drinking water of animals.

BRIEF DESCRIPTION OF THE DRAWINGS

Further preferred features and advantages of the present invention will appear from the following detailed description of some embodiments illustrated with reference to the accompanying drawings in which:

FIG. 3 shows a table of results obtained using complexes of the invention as catalysts.

DESCRIPTION SOME PREFERRED EMBODIMENTS AND EXPERIMENTAL RESULTS

Gold (I) Hydroxide Complexes

The formation of 2 was achieved by use of the reaction of $CsOH.H_2O$ with 1 [Au(IPr)(Cl)] in dichloromethane at room temperature (88% isolated yield). More generally when the conditions of scheme 1 above were employed (a 1:1 solution of THF and toluene for 24 hours at 60° C.), both NaOH and KOH could also be used to produce high yields of the desired [Au(OH)(IPr)] (2) in 92% and 92%, respectively.

The complex 2 [Au(IPr)(OH)] illustrated in Scheme 1 above has been characterised by spectroscopy and by single crystal X-Ray spectroscopy. The $^1H$ NMR of [Au(OH)(IPr)] 2 displays a singlet at 7.12 in $CDCl_3$ and 7.20 in $CD_2Cl_2$ for the two hydrogens of the NHC backbone. (17) In comparison, the NHC protons of [AuCl(IPr)] 1 are shifted 0.07 ppm downfield. The carbenic carbon $^{13}C$ NMR resonance in 2 was found at 171.9 ppm in $CD_2Cl_2$. The presence of a gold-hydroxide fragment is confirmed by a characteristic O—H stretch in the infrared spectrum (3627 $cm^{-1}$).

For X-ray study single crystals were grown by slow diffusion of pentane into a saturated dichloromethane solution containing the complex. The Au to OH bond is covalent in character and the C1 carbon (of the IPr) to Au to O geometry is linear as shown in the representation of the structure derived from the X-Ray data shown in FIG. 1.

Figure 1:
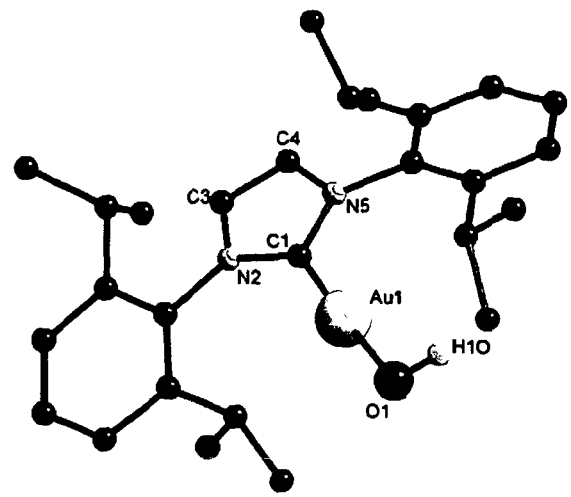
FIG. 1 shows the structure, determined by X-ray of a gold (I) hydroxide complex.

In FIG. 1 most H atoms are omitted for clarity. Selected bond distances (A) and angles (deg), for 2: Au1-O1 2.078 (6), Au1-C1 1.935(6), O1-H1 0.97(2), C1-Au1-O1177.1(3), Au1-O1-H1 111.9(19).

The Au—O1 bond length of 2.078(6) Å shows a covalent bond between the gold and the oxygen atom. The C1-Au1-O1 angle was measured to be 177.1(3) ° as expected for a linear complex.

Reactivity of Gold (1) Hydroxide Complexes

In addition to the reactions discussed above and as illustrated in Scheme 2 complex 2 [Au(OH)(IPr)] has been reacted with fluoroarenes as shown below to provide an estimate of the capability of 2 to undergo protonolysis reactions.

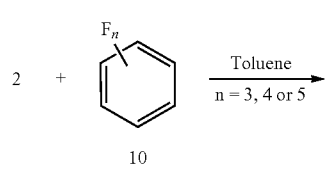

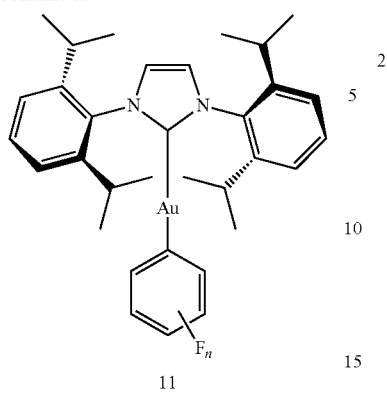

11

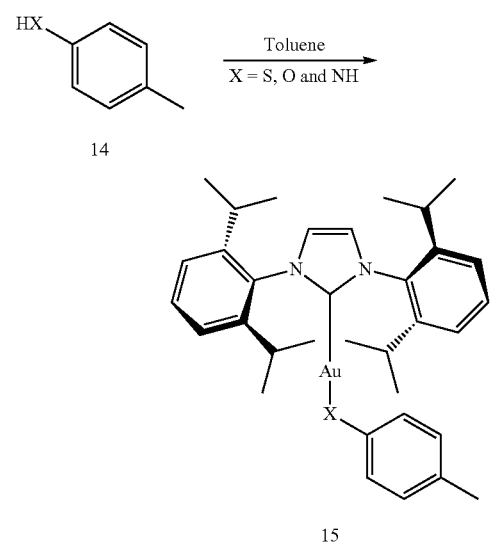

15

Protonolysis reactions involving the fluoroarenes 10 (a-b) [Table 1 below] led to complete conversion of the starting material and conversions into corresponding complexes 11a and 11b in 86 and 93% isolated yields, respectively. In the case of trifluorobenzene 10c, this is however not the case as no reaction was observed and 2 was recovered unchanged. From these reactivity results and the known $pK_a$ (a measure of the acidity of the proton on the substrate) values of the protons on 10, it is estimated that protonolysis reactions involving protons with a $pK_a$ value of up to 29-31 should be successful. (11).

TABLE 1

Deprotonation of some fluoroarenes 10 by [Au(OH)(IPr)] 2.[a]

| entry | fluoroarenes 10 | conditions | $pK_a$[b] | yield (%)[c] |
|---|---|---|---|---|
| 1 | 10a | 60° C., 14 h | 29.0 | 93 |
| 2 | 10b | 80° C., 24 h | 23.1 | 86 |
| 3 | 10c | 80° C., 24 h | 31.5 | 0[d] |

[a]Reaction conditions: [Au(OH)(IPr)] 2 (50 mg, 0.083 mmol), fluoroarenes 10 (0.166 mmol) in toluene (0.8 mL).
[b]Predicted $pK_a$ for fluorobenzenes in DMSO.(25)
[c]Isolated yield.
[d]No conversion.

Further studies comparing reactivity of 2 with thiophenols, phenols and anilines as shown below confirmed the basicity of 2.

TABLE 2

Formation of heteroatom-gold bonds from [Au(OH)(IPr)] 2.[a]

| Entry | Substrates 14 | Conditions | Yield(%)[b] Products 15 a-c |
|---|---|---|---|
| 1 | 14a | RT, 14 h | 96 |
| 2 | 14b | 60° C., 14 h | 89 |
| 3 | 14c | 100° C., 24 h | 85 |

[a]Reaction conditions: [Au(OH)(IPr)] 2 (0.05 mmol), substrates 14 (0.05 mmol) in toluene (0.5 mL).
[b]Isolated yield of products 15a-15c.

The proton borne by the heteroatom of p-thiocresol (14a), with a $pK_a$ of 10.3, (26) readily reacts with 2 at RT leading to high isolated yields of 15a. The less acidic proton of p-cresol (14b), $pK_a$ of 18.9, (12) is still well below the estimated limiting value of 29 to 31 and formation of 15b is observed cleanly. The most challenging p-toluidine (14c) with a $pK_a$ estimated at 30 (13) required much more forceful conditions and temperatures leading to the elimination of water and formation of 15c.

Dinuclear Gold Complexes

Complex 12 {Au(IPr)}$_2$(μ-OH)]BF$_4$ depicted below can be made by various routes.

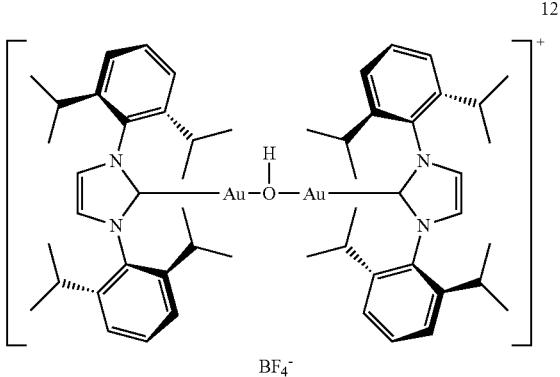

Manufacture from 13 [Au(IPr)(CH₃CN)]BF₄ by stirring in water at 60° C. for 3 days in air leads to the formation of 12 in high yield. The simple attempted extraction of 12 from an aqueous mother reaction with DCM proved problematic, as 12 converts back to 13 under this straightforward operation. Satisfactory isolation of 12 was achieved by washing the organic phase with water followed by collection of the insoluble product by filtration.

A more economical and practical synthetic route is to take advantage of [Au(IPr)(OH)] 2 and its straightforward reaction with 0.5 equiv. HBF$_4$.OEt$_2$ in benzene for 4 h at room temperature to produce 12 in 90% isolated yield.

Complex 12 {Au(IPr)}$_2$(μ-OH)]BF$_4$ can also be made starting from [Au(IPr)Cl]. After abstraction of chloride with AgBF$_4$, to formally generate the putative [Au(IPr)]$^+$BF$_4^-$ species, and removal of precipitated AgCl by filtration through Celite, the organic phase was washed three times with water. Recrystallisation from DCM/pentane afforded 12 in 81% yield.

[Au(IPr)(OH)] 2 can also be successfully used in the synthesis of [Au(IPr)(CH₃CN)]BF$_4$ 13 under anhydrous conditions and without the use of costly and light- and moisture-sensitive silver salts. Complex 2 is simply reacted with one equivalent of HBF$_4$.OEt$_2$ in the presence of 1 equiv. of acetonitrile to afford complete conversion into 13.

Detailed Synthetic Methods for 12 {Au(IPr)}$_2$(μ-OH)]BF$_4$ and 13 [(Au(IPr)(CH₃CN)]BF$_4$ 12 Route A: 13 [Au(IPr)(CH₃CN)BF$_4$ (2 g, 2.80 mmol) was suspended in water (3 ml, 167 mmol) and stirred at 60° C. for 72 h in air. The reaction mixture was extracted with DCM and the organic phase was washed 4 times with a large excess of water and dried over MgSO$_4$. The mixture was filtered and the volatiles were evaporated under reduced pressure. The resulting white crude product was recrystallised from CH$_2$Cl$_2$/pentane to give 1.71 g (96%) of a white microcrystalline solid.

12 Route B: 2 [Au(IPr)(OH)] (97 mg, 0.160 mmol) was dissolved in benzene (2 mL) and tetrafluoroboric acid-diethyl ether complex (11.0 μL, 0.080 mmol) was added by syringe. The reaction mixture was stirred 4 h at room temperature. Pentane was added to the reaction to precipitate the product as a white solid. The crude white product was recrystallised from CH$_2$Cl$_2$/pentane to give 92 mg (90%) of a white microcrystalline solid.

$^1$H NMR (400 MHz, CDCl$_3$): δ 7.50 (t, J=7.8 Hz, 4H), 7.26 (s, 4H), 7.24 (d, J=7.8 Hz, 8H), 2.39 (sept, J=6.9 Hz, 8H), 1.19 (d, J=6.9 Hz, 24H), 1.11 (d, J=6.9 Hz, 24H). $^{13}$C NMR (75 MHz, CDCl$_3$): δ 162.6, 145.4, 133.6, 130.7, 124.4, 124.2, 124.1, 28.6, 24.4, 23.8. $^{19}$F NMR (185 Hz): δ −154.90, −154.85. IR (cm$^{-1}$): 3621, 3167, 3137, 3084, 2964, 2928, 2871, 1596, 1553, 1472, 1421, 1386, 1365, 1329, 1215, 1058, 947, 807, 762, 707, 581, 455. Elemental Analysis (calc): C, 51.06 (50.87), H, 5.27 (5.77), N, 4.36 (4.39).

Synthesis of [(Au(IPr)(CH₃CN)]BF$_4$ 13 from 2:

[Au(IPr)(OH)] (100 mg, 0.166 mmol) was dissolved in toluene (2 mL) and tetrafluoroboric acid-diethyl ether complex (0.023 mL, 0.166 mmol) was added by syringe. Then, acetonitrile (8.67 μL, 0.166 mmol) was added and the heterogeneous reaction mixture was stirred 2 h at room temperature. Pentane was added to precipitate 114 mg (96%) of a white microcrystalline solid whose NMR data confirms the synthesis of 13. $^1$H NMR (400 MHz, CDCl$_3$): δ 7.58 (t, J=7.8 Hz, 2H), 7.38 (s, 2H), 7.34 (d, J=7.8 Hz, 4H), 2.44 (sept, J=6.9 Hz, 4H), 2.39 (s, 3H), 1.29 (d, J=6.9 Hz, 12H), 1.24 (d, J=6.9 Hz, 12H). $^{13}$C NMR (100 MHz, CDCl$_3$): δ 166.3, 145.5, 133.0, 131.5, 124.8, 124.6, 121.0, 28.9, 24.7, 24.0, 2.7. $^{19}$F NMR (185 Hz): δ −154.98, −153.92.

Structure of 12

Figure 2:
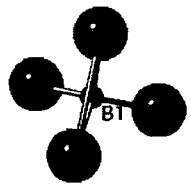
FIG. 2 shows the structure, determined by X-ray of a digold complex of the invention.
Figure 2:
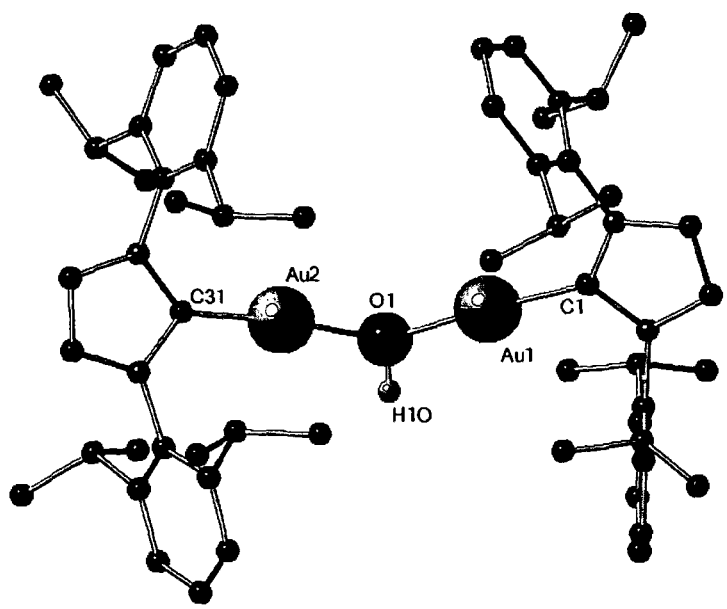

The complex 12 {Au(IPr)}$_2$(μ-OH)]BF$_4$ was shown to have the structure shown in FIG. 2, by X-ray determination.

Selected bond lengths [Å] and angles [deg] of the structure of 12 are: Au1-Au2 3.746(1); Au1-O1, 2.070(5); Au2-O1, 2.072(5); Au1-C1, 1.957(7); Au2-C31, 1.948(7); Au1-O1-Au2, 129.5(3); O1-H10, 0.97(2); Au1-O1-H10, 105(5); Au2-O1-H10, 107(5); C1-Au1-O1, 174.2(2); C31-Au2-O1, 173.8(2). DFT values: Au—Au 3.886; Au—O, 2.081; Au—C, 1.974; O—H, 0.976; Au—O—Au, 137.9; Au—O—H, 109.7.

The Au1-C1 (1.957(7) Å) and the Au2-C31 bond (1.948 (7) Å) distances are longer than that found in 2 (1.935(6) Å). The Au1-Au2 distance found in 12 is 3.746 Å, which is in the range of van der Waals interactions. Complex 12 is reminiscent of the dinuclear [{(Ph$_3$P)Au}$_2$Br]BF$_4$ complex reported by Schmidbaur and co-workers where a Au—Br bond length of 2.4384(6) Å and a Au—Au distance of 3.6477(1) Å are found. (14,15)

Catalytic Activity of Gold (I) Hydroxide Complexes and Dinuclear Gold Hydroxide Complexes A Hydration of Nitriles

[Au(IPr)(OH)] 2 was tested in the hydration of benzonitrile to benzamide at 140° C. in aqueous media (microwave heating) resulted in a yield of 23% after 1 hour. In comparison 2.5 mol % of 12 {Au(IPr)}$_2$(μ-OH)]BF$_4$ resulted in a 87% conversion after 15 minutes and the conversion reached 96% after 30 min.

This compares favourably with the use of the known catalyst [Au(IPr)(NTf$_2$)] (16 NTf$_2$=bis(trifluoromethanesulfonyl)imidate) where 5 mol % gave, after 15 min at 140° C., a 54% conversion of benzonitrile into benzamide.

Results obtained using isolated 12 are summarised in Table 3 below, with the reactions carried out using the following general procedure.

In a typical reaction, [Au(IPr)(NTf$_2$)] (13 mg, 20 μmol, 2 mol %) or [{Au(IPr)}$_2$(μ-OH)]BF$_4$ (17 mg, 10 μmol, 1 mol %) was added to THF (0.5 mL) in a 2 mL microwave vial in air. Benzonitrile (103 mg, 1 mmol) was added, followed by distilled H$_2$O (500 μL). The vial was sealed and heated in the microwave for 2 h at 140° C. (7 bar). The conversion was determined by gas chromatography.

TABLE 3 nitrile hydrolysis catalysed by 12 or 16

Ar—≡ →[12 {Au(IPr)}$_2$(μ-OH)]BF$_4$ (1 mol %) or 16 [Au(IPr)(NTf2)] (2 mol %)][THF:H$_2$O 1:1, MW 2 hrs 140 C.] Ar—C(=O)NH$_2$

| Entry | Substrate | Product | Conv. with 12 | Conv. with 16 |
|---|---|---|---|---|
| 1 | benzonitrile | benzamide | 98% | 99% |
| 2 | 3-methylbenzonitrile | 3-methylbenzamide | 97% | 82% |
| 3 | 4-methoxybenzonitrile | 4-methoxybenzamide | 94% | 76% |
| 4 | 3,5-difluorobenzonitrile | 3,5-difluorobenzamide | 100% | 100% |
| 5 | 3-phenylpropanenitrile | 3-phenylpropanamide | 90%[a] | 30%[b] |
| 6 | isonicotinonitrile | isonicotinamide | 75%[c] | 31%[d] |

[a] 2.5 mol % of 12
[b] 5 mol % of 16
[c] 2.5 mol % of 12, 6 h
[d] 5 mol % of 16, 6 h.

An in situ preparation of 12 {Au(IPr)}$_2$(μ-OH)]BF$_4$ from 2 [Au(IPr)(OH)] provides equally good results. The addition of 0.5 equiv. of HBF$_4$.OEt$_2$ (with respect to gold) to a reaction mixture containing 2 and substrates leads to an identical catalytic conversion as when pre-isolated 12 is employed.

Catalysis by the use of isolated 12 or by in situ preparation of 12 is further illustrated by the reactions B to I below.

B Skeletal Rearrangement of Enynes

In dry dichloromethane, following the procedure of Echavarren (16), a skeletal rearrangement was observed with complete conversion in 25 minutes at room temperature. No silver compound is required as in the prior art.

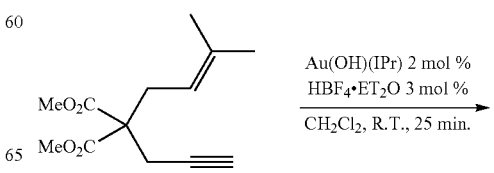

-continued

C Alkoxycyclisation of Enynes

This reaction was previously reported by Echavarren (17) with Au(Me)(PPh₃) (3 mol %) and HBF₄ (6 mol %) in 4 h at room temperature. Gagosz (18) has also reported this alkoxycyclization with several catalyst generated in-situ. The best previous result was obtained with a cationic gold complex bearing X-Phos and SbF₆ as a counter anion. The results with the in situ generation of 12 {Au(IPr)}₂(µ-OH)]BF₄ are excellent and the reaction is much easier to carry out.

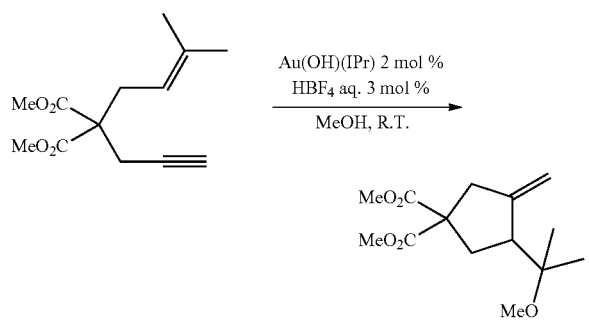

D Alkyne Hydration

For this reaction the use of 5 mol % of Au(IPr)Cl and 10 mol % of AgSbF₆ in a mixture of dioxane/water (2:1) at 80° C. for 1 h30 has been previously reported (19). Tanaka reported another acid activation of a gold precursor (20). 1 mol % of [Au(PPh₃)Me] with H₂SO₄ 50 mol % in methanol/water (2/1 to 6/1) at 70° C. for 5 h gave a 53% isolated yield. The present method does not require silver and is relatively straightforward to carry out.

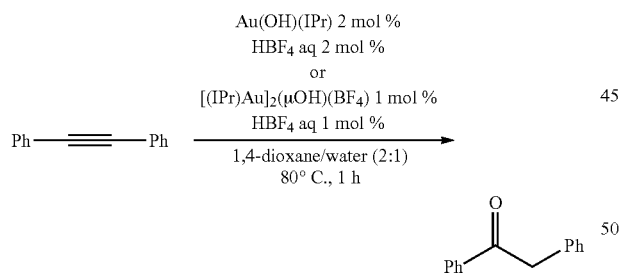

E Meyer-Schuster Reaction

For the Meyer-Schuster reaction, the use of 2 mol % of [(IPr)AuCl]/AgSbF₆ in the mixture of MeOH/water at 60° C. overnight has previously been reported (21). The reaction can now be done without silver.

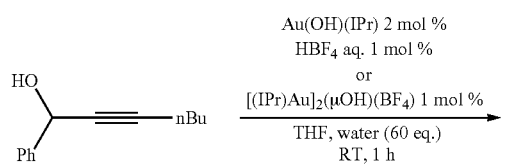

-continued

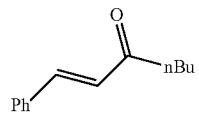

F 3,3' Rearrangement of Allylic Acetates

The use of 3 mol % of [(IPr)AuCl] and 2 mol % of AgBF₄ in DCE at 80° C. for 12 min. has been reported previously (22). The method below does not require the use of silver co-catalyst/activator

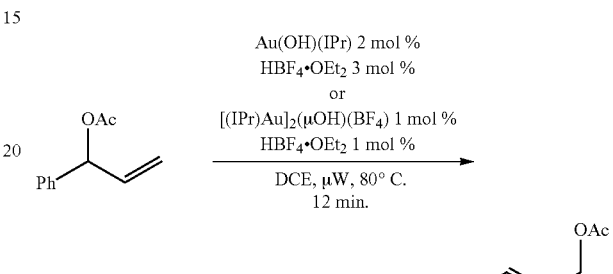

G Cyclisation of Propargylic Acetate

Previously, the use of 2 mol % of [(IPr)AuCl] and 2 mol % of AgBF₄ in DCM at room temperature for 12 min, has been reported (23). Again no silver is required by using 12 (generated in situ).

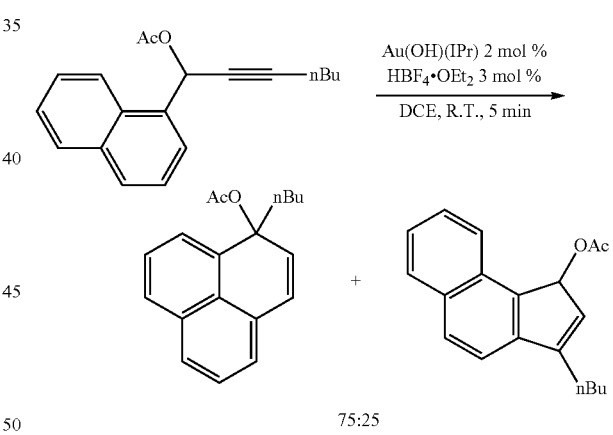

75:25

H Beckman Type Rearrangement

Previously 5 mol % of Au(IPr)Cl and 10 mol % of AgBF₄ neat at 100° C. for 20 h has been employed (24). It had been assumed that silver played a role in the mechanism. This reaction is now done without silver.

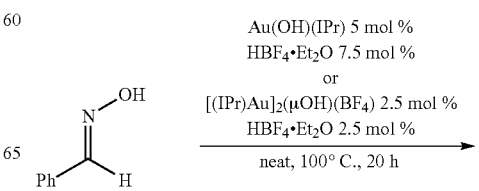

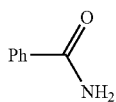

I Hydroamination

Widenhoefer used several conditions to achieve this reaction: [Au(PPh$_3$)Cl] 5 mol % with AgOTf 5 mol % in dioxane at 60° C. for 18 h. (25) [Au(IPr)Cl] 5 mol % with AgOTf 5 mol % in dioxane at 45° C. for 15 h. (26)

No silver is required when using 12 or 12 generated in situ from 2.

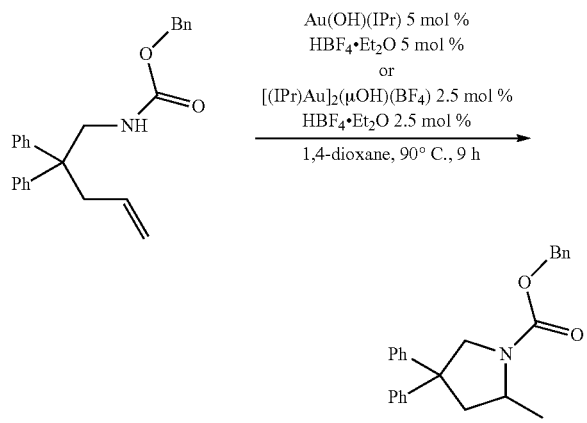

A summary of results for reactions A to I are given in Table 4 (FIG. 1), where AuOH refers to the use of 2 [Au(IPr)(OH)] (with in situ generation of 12 where HBF$_4$ is employed) and where Au$_2$(μOH) refers to the use of 12 {Au(IPr)}$_2$(μ-OH)]BF$_4$, previously isolated and added to the reaction mixture.

Activity of Gold Hydroxide Complexes Against Human Cancer Cells

The gold hydroxide complexes of the present invention have been evaluated for their cytotoxicity towards human cancer cell lines.

The IC$_{50}$ and IC$_{10}$ concentrations for the complex 2 were tested using the LNCaP (prostate carcinoma), MDA MB231 (breast carcinoma) and B42 CL16 (breast carcinoma) cell lines as shown below.

| IC$_{50}$ (μM) LNCaP | IC$_{10}$ (μM) LNCaP | IC$_{50}$ (μM) MDA MB231 | IC$_{10}$ (μM) MDA MB231 | IC$_{50}$ (μM) B42 CL16 | IC$_{10}$ (μM) B42 CL16 |
|---|---|---|---|---|---|
| 1.40 | 2.30 | 0.90 | 1.42 | 0.18 | 0.41 |

Activity of 2 towards a human urothelial cell line (SV-HUC-1) and a bladder carcinoma cell line (MGH-U1) was also measured and results given below.

| IC$_{50}$ (μM) SV-HUC-1 | IC$_{10}$ (μM) SV-HUC-1 | IC$_{50}$ (μM) MGH-U1 | IC$_{10}$ (μM) MGH-U1 |
|---|---|---|---|
| 0.10 | 0.35 | 0.18 | 0.45 |

Activity of 2 towards a human prostate epithelial cell line P21TZ and a prostate carcinoma cell line P21PZ derived from the same patient are also shown below.

| IC$_{50}$ (μM) P21TZ | IC$_{10}$ (μM) P21TZ | IC$_{50}$ (μM) P21PZ | IC$_{10}$ (μM) P21PZ |
|---|---|---|---|
| 0.43 | 0.82 | 0.35 | 0.50 |

The cytotoxicity of anti-cancer drug cisplatin was also evaluated against three of these cell lines for comparison purposes as below. These results show that complex 2 has much lower IC$_{50}$ values than cisplatin.

| Cell Line | SV-HUC-1 | LNCaP | MDA MB231 |
|---|---|---|---|
| IC$_{50}$ (μM) | 25 | 18 | 28 |

The well-established prostate and breast cancer lines (LNCaP and MDA MB231) were less sensitive than the bladder cell lines (SV-HUC-1 and MGH-U1) which in turn had a similar sensitivity to the prostate and breast cell lines (B42 CL16 and P21TZ and P21 PZ). There were only small differences between the sensitivity of the normal epithelial cells and tumour cells derived from the same patient. Overall activity of 2 was superior to that displayed by cisplatin.

Test Protocol

Cytotoxicity assay: The compound/complex was dissolved in DMSO and diluted in DMSO. The final dilution was in the respective culture medium and the final concentration of DMSO was always below 0.01%. Cells were pipetted into microtitre plates (NUNC) at 4000 cells/well and incubated at 37° C. in 5% CO$_2$ in air for 24 hr. Varying concentrations of the compounds/complexes were applied to the cells in 10 μl volumes. The plates were incubated for 3 days at 37° C. 5% CO$_2$ in air. The viability of the cells was measured using the Dojindo kit CCK-8 (Cell counting Kit—8, Dojindo technologies USA, CK04-11) method after incubation for 3 hr in the absence of light. The plates were read on an ELISA plate reader at a wavelength of 450 nm.

REFERENCES

1. H. W. Roesky, S. Singh, K. K. M. Yusuff, J. A. Maguire, N. S. Hosmane, Chem. Rev. 106, 3813 (2006).
2. a) G. Marcon, S. Carotti, M. Coronnello, L. Messori, E. Mini, P. Orioli, T. Mazzei, M. A. Cinellu, G. Minghetti, J. Med. Chem. 45, 1672 (2002); b) M. A. Cinellu, G. Minghetti, M. V. Pinna, S. Stoccoro, A. Zucca, M. Manassero, Eur. J. Inorg. Chem. 2304 (2003).
3. a) Z. Li, C. Brouwer, C. He, Chem. Rev. 2008, 108, 3239; b) A. Arcadi, Chem. Rev. 108, 3266 (2008); c) E. Jimenez-Nunez, A. M. Echavarren, Chem. Rev. 108, 3326 (2008).
4. a) K. M. Hindi, M. J. Panzner, C. L. Cannon, W. J. Youngs, Chem. Rev. 2009, 109, 3859; b) H. G. Raubenheimer, S. Cronje, Chem. Soc. Rev. 37, 1998 (2008).
5. a) N. M. Scott, S. P. Nolan, Eur. J. Inorg. Chem. 2005, 1815; b) D. J. Gorin, B. D. Sherry, F. D. Toste, Chem. Rev. 108, 3351 (2008).
6. a) F. Glorius Ed. N-Heterocyclic Carbenes in Transition Metal Catalysis; Springer-Verlag: Berlin, Germany, 2007. b) S. P. Nolan Ed. N-Heterocyclic Carbenes in Synthesis; Wiley-VCH: Weinheim, Germany, 2006; c) F. E. Hahn, M. C. Jahnke, Angew. Chem., Int. Ed. 47, 3122 (2008); d) N. Marion, S. P. Nolan, Chem. Soc. Rev. 2008, 37, 1776; e) S. Diez-Gonzalez, N. Marion, S. P. Nolan, Chem. Rev. 109, 3612 (2009).

7. D. V. Partyka, M. Zeller, A. D. Hunter, T. G. Gray, Angew. Chem., Int. Ed. 45, 8188 (2006).
8. G. A. Molander; B. Canturk, Angew. Chem., Int. Ed. 48, 9240 (2009).
9. E. Y. Tsui, P. Müller, J. P. Sadighi, Angew. Chem., Int. Ed. 47, 8937 (2008).
10. a) N. Mezailles, L. Ricard, F. Gagosz, Org. Lett. 7, 4133 (2005); b) L. Ricard, F. Gagosz, Organometallics 26, 4704 (2007).
11. K. Shen, Y. Fu, J.-N. Li, L. Liu, Q.-X. Guo, Tetrahedron 63, 1568 (2007).
12. F. G. Bordwell, R. J. McCallum, W. N. Olmstead, J. Org. Chem. 49, 1424 (1984).
13. $pK_a$ for m-toluidine, see: L. K. Blair, J. Baldwin, W. C. Smith, Jr., J. Org. Chem. 42, 1817 (1977).
14. A. Bayler, A. Bauer, H. Schmidbaur, Chem. Ber. 1997, 130, 115-118.
15. For structural comparison with a Pt congener, [{PtPh(cod)}$_2$(μ-OH)]BF$_4$ see: Y. Suzaki, K. Osakada, Organometallics 2004, 23, 5081-5084.
16. Nieto-Oberhuber, C.; Paz Munoz, M.; Buñuel, E.; Nevado, C.; Cardenas, D. J.; Echavarren, A. M. Angew. Chem. Int. Ed. 2004, 43, 2402-2406.
17. Nieto-Oberhuber, C.; Paz Muñoz, M.; Buñuel, E.; Nevado, C.; Cárdenas, D. J.; Echavarren, A. M. Angew. Chem. Int. Ed. 2004, 43, 2402-2406.
18. Mézailles, N.; Ricard, L.; Gagosz, F. Org. Let. 2005, 7, 4133-4136.
19. Marion, N.; Ramón, R. S.; Nolan, S. P. J. Am. Chem. Soc. 2009, 131, 448-449.
20. Mizushima, E.; Sato, K.; Hayashi, T.; Tanaka, M. Angew. Chem., Int. Ed. 2002, 41, 4563-4565.
21. Ramón, R. S.; Marion, N.; Nolan, S. P. Tetrahedron 2009, 65, 1767-1773.
22. Marion, N.; Gealageas, R.; Nolan, S. P. Org. Lett. 2007, 9, 2653-2656.
23. Marion, N.; Diez-González, S.; de Frémont, P.; Noble, A. R.; Nolan, S. P. Angew. Chem., Int. Ed. 2006, 45, 3647-3650.
24. Ramón, R. S.; Bosson, J.; Diez-González, S.; Marion, N.; Nolan, S. P. J. Org. Chem. 2010, DOI: 10.1021/jo902461a
25. Han, X.; Widenhoefer, R. A. Angew. Chem. Int. Ed. 2006, 45, 1747-1749.
26. Bender, C. F.; Widenhoefer, R. A. Org. Lett. 2006, 8, 5303-5305.
27. Marion, N.; Carlqvist, P.; Gealageas, R.; de Fremont, P.; Maseras, F.; Nolan, S. P.; Chem. Eur. J. 2007, 13, 6437-6451.
28. Sharp, P. R.; Yang, Y.; J. Am. Chem. Soc. 1994, 116, 6983-6984.
29. Kissner, R.; Welti, G.; Geier, G.; J. Chem. Soc., Dalton Trans., 1997, 1773-1777.

The invention claimed is:

1. A method of catalyzing a chemical transformation, the method comprising:
contacting a gold (I) hydroxide complex of the form Z—Au—OH; or
a digold (I) hydroxide complex according to general formula V:

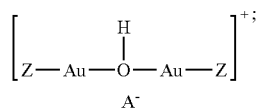

(V)

wherein the groups Z are the same for each occurrence or that are different for each occurrence and are nitrogen containing heterocyclic carbene ligands of the form:

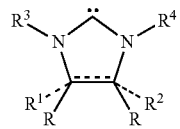

wherein the groups R, R$^1$ R$^2$, R$^3$ and R$^4$ are the same or different and the dashed line in the ring represents optional unsaturation, wherein W and R$^2$ are absent; and wherein each R and R$^1$, R$^2$, R$^3$ and R$^4$ are, independently for each occurrence, selected from: H; substituted or unsubstituted primary or secondary alkyl group; substituted or unsubstituted phenyl; substituted or unsubstituted naphthyl; substituted or unsubstituted anthracenyl; or a functional group selected from the group consisting of: halo, hydroxyl, sulfhydryl, cyano, cyanato, thiocyanato, amino, nitro, nitroso, sulfo, sulfonato, boryl, borono, phosphono, phosphonato, phosphinato, phospho, phosphino, and silyloxy; and A$^-$ is an anion, with a substrate; and chemically transforming the substrate;

wherein the complex is used as a catalyst, or for the in situ production of a catalyst, for catalyzing a chemical transformation of the substrate, the chemical transformation selected from the group consisting of: hydration of nitriles, skeletal arrangement of enynes, alkoxycyclisation of enynes, alkyne hydration, the Meyer-Shuster reaction, 3,3' rearrangement of allylic acetates, cyclisation of propargylic acetates, Beckman rearrangements and hydroamination.

2. The method according to claim 1 wherein the complex is according to general formula V and the anion A$^-$ is selected from the group consisting of BF$_4^-$, PF$_6^-$, SbF$_6^-$, [B{C$_6$H$_3$(CF$_3$)$_2$}$_4$]$^-$, and [B(C$_6$F$_5$)$_4$]$^-$.

3. The method according to claim 1 wherein the nitrogen containing heterocyclic carbene ligands have a structure according to any one of the following formulas I to IV:

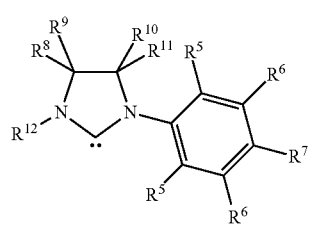

I

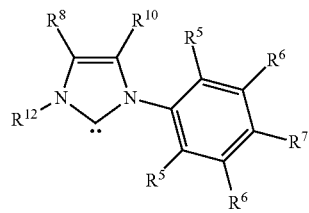

II

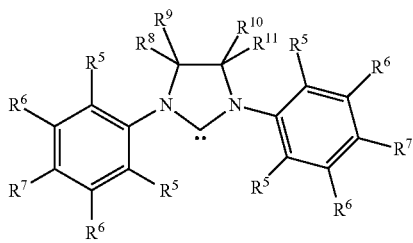

III

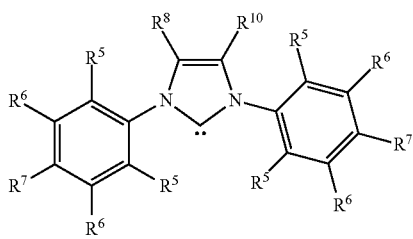

IV wherein each group $R^5$, $R^6$ and $R^7$, is independently for each occurrence selected from: H, a primary or secondary alkyl group that is substituted or unsubstituted, substituted or unsubstituted phenyl, substituted or unsubstituted naphthyl, or substituted or unsubstituted anthracenyl, or a functional group selected from the group consisting of halo, hydroxyl, sulfhydryl, cyano, cyanato, thiocyanato, amino, nitro, nitroso, sulfo, sulfonato, boryl, borono, phosphono, phosphonato, phosphinato, phospho, phosphino, and silyloxy;

$R^8$, $R^9$, $R^{10}$ and $R^{11}$ are each independently for each occurrence H, a substituted or unsubstituted alkyl group, substituted or unsubstituted aryl, or in formulas (II) and (IV) together with the carbons carrying them form a substituted or unsubstituted, fused 4-8 membered carbocylic ring or a substituted or unsubstituted, fused aromatic ring, preferably a fused phenyl ring; and $R^{12}$ is alkyl or a cycloalkyl.

4. The method according to claim 3 wherein the nitrogen containing heterocyclic carbene ligands have a structure according to any one of the following formulas:

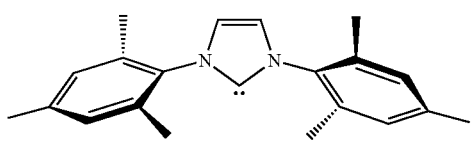

IMes

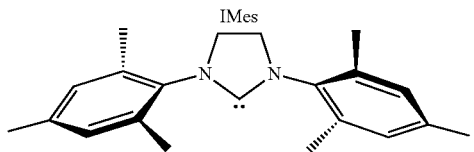

SIMes

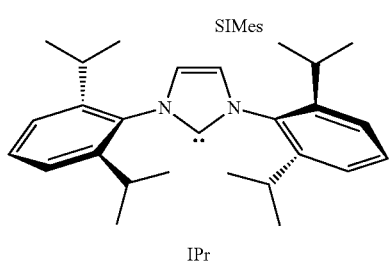

IPr

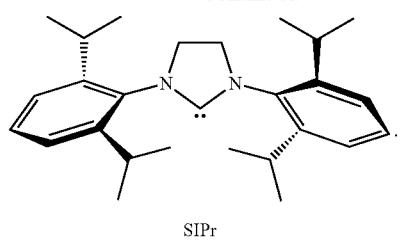

SIPr

5. The method according to claim 1 wherein the gold hydroxide complex has the structural formula:

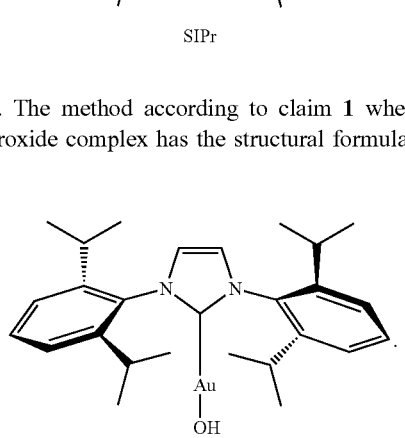

6. The method according to claim 1 wherein the gold hydroxide complex has the structural formula:

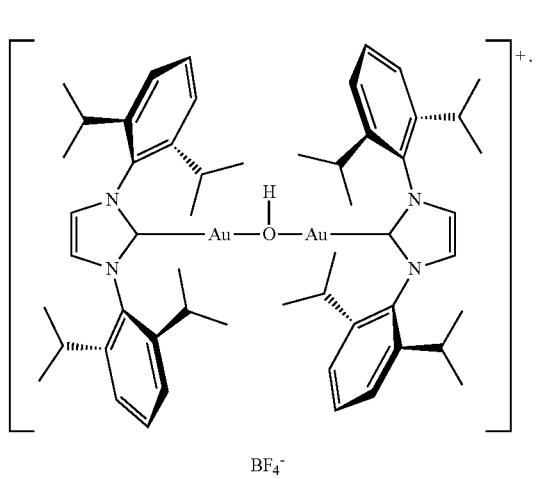

BF$_4^-$

7. A gold (I) hydroxide complex of the form Z—Au—OH;

or a digold (I) hydroxide complex according to general formula V:

(V)

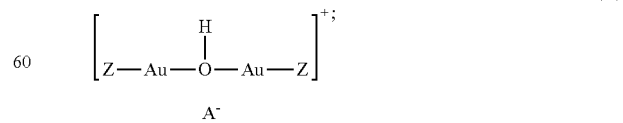

A$^-$ wherein the groups Z are the same or different for each occurrence and are nitrogen containing heterocyclic carbene ligands of the form:

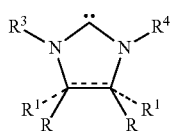

wherein the groups R, $R^1$ $R^2$, $R^3$ and $R^4$ are the same or different and the dashed line in the ring represents optional unsaturation, wherein $R^1$ and $R^2$ are absent; and wherein each R and $R^1$, $R^2$, $R^3$ and $R^4$ are, independently for each occurrence, selected from: H; substituted or unsubstituted primary or secondary alkyl group; substituted or unsubstituted phenyl; substituted or unsubstituted naphthyl; substituted or unsubstituted anthracenyl, with the proviso that for the Z—Au—OH complex both $R^3$ and $R^4$ are not methyl or ethyl when $R^1$ and $R^2$ are absent and R is H; or a functional group selected from the group consisting of: halo, hydroxyl, sulfhydryl, cyano, cyanato, thiocyanato, amino, nitro, nitroso, sulfo, sulfonato, boryl, borono, phosphono, phosphonato, phosphinato, phospho, phosphino, and silyloxy; and $A^-$ is an anion.

8. The complex of claim 7 wherein the complex is according to general formula V and the anion $A^-$ is selected from the group consisting of $BF_4^-$, $PF_6^-$, $SbF_6^-$, $[B\{C_6H_3(CF_3)_2\}_4]^-$ and $[B(C_6F_5)_4]^-$.

9. The complex of claim 7 wherein the nitrogen containing heterocyclic carbene ligands have a structure according to any one of the following formulas I to IV:

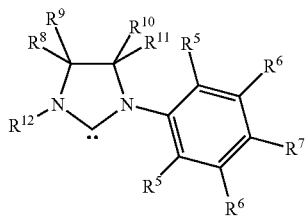

I

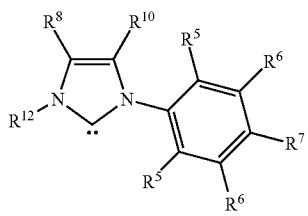

II

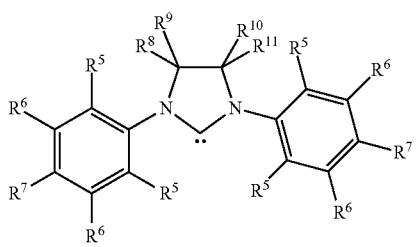

III

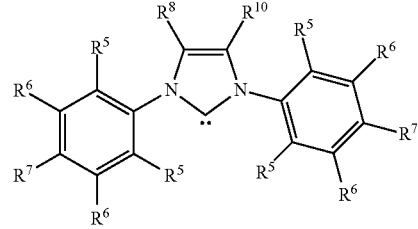

IV wherein each group $R^5$, $R^6$ and $R^7$, is independently for each occurrence selected from: H, a primary or secondary alkyl group that is substituted or unsubstituted, substituted or unsubstituted phenyl, substituted or unsubstituted naphthyl, or substituted or unsubstituted anthracenyl, or a functional group selected from the group consisting of halo, hydroxyl, sulfhydryl, cyano, cyanato, thiocyanato, amino, nitro, nitroso, sulfo, sulfonato, boryl, borono, phosphono, phosphonato, phosphinato, phospho, phosphino, and silyloxy;

$R^8$, $R^9$, $R^{10}$ and $R^{11}$ are each independently for each occurrence H, a substituted or unsubstituted alkyl group, substituted or unsubstituted aryl, or in formulas (II) and (IV) together with the carbons carrying them form a substituted or unsubstituted, fused 4-8 membered carbocylic ring or a substituted or unsubstituted, fused aromatic ring, preferably a fused phenyl ring; and $R^{12}$ is alkyl or a cycloalkyl.

10. The complex of claim 9 wherein the nitrogen containing heterocyclic carbene ligands have a structure according to any one of the following formulas:

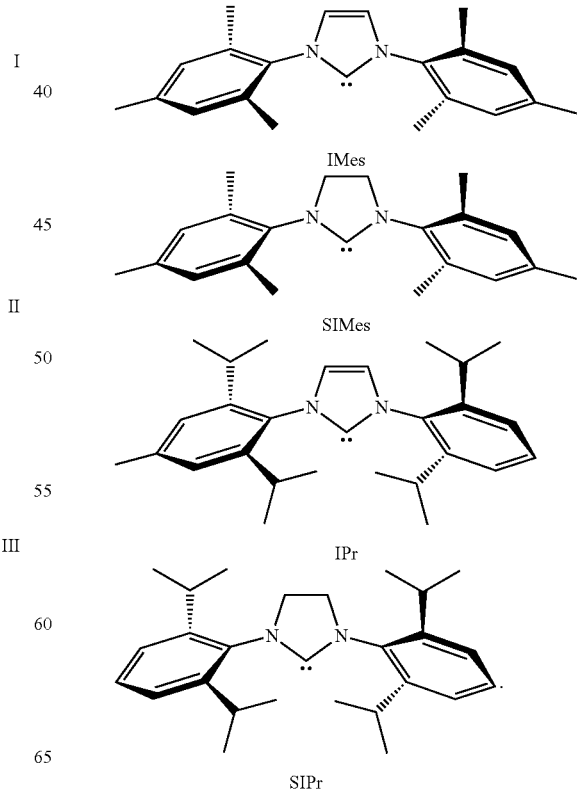

11. The complex of claim 7 having the structural formula:

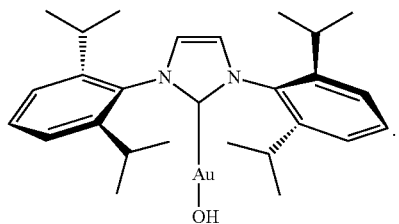

12. The complex of claim 7 having the structural formula:

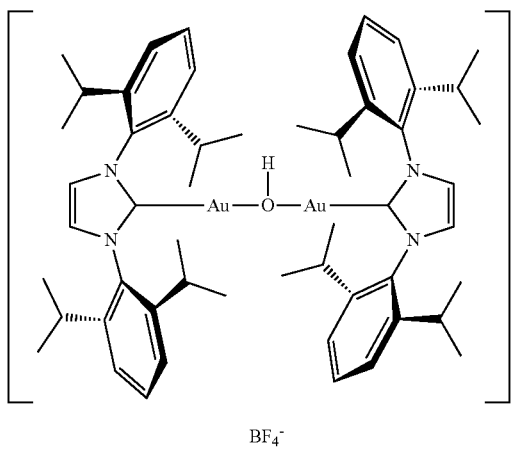

13. A pharmaceutical formulation comprising a gold (I) hydroxide complex of the form Z—Au—OH or a digold (I) hydroxide complex according to general formula V:

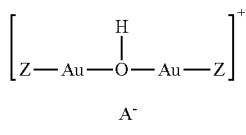
(V)

wherein the groups Z are the same or different for each occurrence and are nitrogen containing heterocyclic carbene ligands of the form:

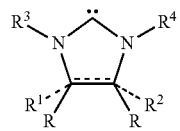

wherein the groups R, $R^1$ $R^2$, $R^3$ and $R^4$ are the same or different and the dashed line in the ring represents optional unsaturation, wherein $R^1$ and $R^2$ are absent; and wherein each R and $R^1$, $R^2$, $R^3$ and $R^4$ are, independently for each occurrence, selected from: H; substituted or unsubstituted primary or secondary alkyl group; substituted or unsubstituted phenyl; substituted or unsubstituted naphthyl; substituted or unsubstituted anthracenyl; with the proviso that for the Z—Au—OH complex both $R^3$ and $R^4$ are not methyl or ethyl when $R^1$ and $R^2$ are absent and R is H; or a functional group selected from the group consisting of: halo, hydroxyl, sulfhydryl, cyano, cyanato, thiocyanato, amino, nitro, nitroso, sulfo, sulfonato, boryl, borono, phosphono, phosphonato, phosphinato, phospho, phosphino, and silyloxy; and $A^-$ is an anion; or a physiologically acceptable salt, ester or other physiologically functional derivative of the complex of the form Z—Au—OH or of the complex according to formula V together with one or more pharmaceutically acceptable carriers.

* * * * *

UNITED STATES PATENT AND TRADEMARK OFFICE
CERTIFICATE OF CORRECTION

PATENT NO.         : 9,464,097 B2
APPLICATION NO.    : 13/580772
DATED              : October 11, 2016
INVENTOR(S)        : Steven P. Nolan It is certified that error appears in the above-identified patent and that said Letters Patent is hereby corrected as shown below:

In the Claims

In column 26, claim 1, please change line 11 to:

"optional unsaturation, wherein $R^1$ and $R^2$ are absent;"

In column 29, image in line 5, please change to:

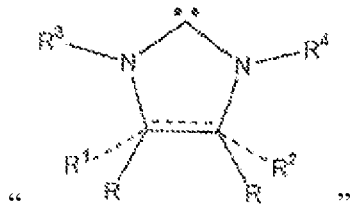

In column 30, image in lines 50-55, please change to:

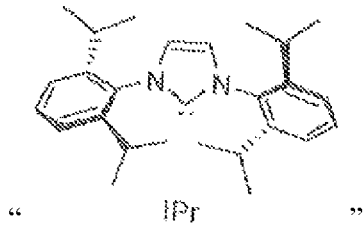

Signed and Sealed this
Twentieth Day of December, 2016

Michelle K. Lee
*Director of the United States Patent and Trademark Office*